(12) United States Patent
Oseko

(10) Patent No.: US 7,932,472 B2
(45) Date of Patent: Apr. 26, 2011

(54) MEASUREMENT APPARATUS FOR MEASURING CHANGES IN BODY COMPOSITION

(75) Inventor: Naoshi Oseko, Itabashi-ku (JP)

(73) Assignee: Tanita Corporation, Itabashi-Ku, Tokyo (JP)

( * ) Notice: Subject to any disclaimer, the term of this patent is extended or adjusted under 35 U.S.C. 154(b) by 249 days.

(21) Appl. No.: 12/172,568

(22) Filed: Jul. 14, 2008

(65) Prior Publication Data

US 2009/0057035 A1 Mar. 5, 2009

(30) Foreign Application Priority Data

Sep. 4, 2007 (JP) ................................. 2007-228894

(51) Int. Cl.
G01G 19/44 (2006.01)
(52) U.S. Cl. .................. 177/25.16; 177/25.19; 128/921; 600/547
(58) Field of Classification Search ............... 177/25.16, 177/25.19, 177; 600/547; 128/921
See application file for complete search history.

(56) References Cited

U.S. PATENT DOCUMENTS

| | | | | |
|---|---|---|---|---|
| 3,655,003 | A * | 4/1972 | Yamajima | 177/173 |
| 4,149,605 | A | 4/1979 | Mettler et al. | |
| 4,461,301 | A * | 7/1984 | Ochs | 600/301 |
| 4,650,014 | A * | 3/1987 | Oldendorf et al. | 177/177 |
| 4,773,492 | A * | 9/1988 | Ruzumna | 177/25.19 |
| 5,463,192 | A | 10/1995 | Wirth et al. | |
| 6,538,215 | B2 * | 3/2003 | Montagnino et al. | 177/25.16 |
| 6,694,126 | B1 * | 2/2004 | Van Lente | 455/66.1 |
| 6,816,071 | B2 * | 11/2004 | Conti | 340/540 |
| 7,130,617 | B2 * | 10/2006 | Matsumoto et al. | 455/412.2 |
| 7,265,301 | B2 * | 9/2007 | Simberg | 177/25.13 |
| 7,440,748 | B2 * | 10/2008 | Matsumoto et al. | 455/412.2 |
| 7,557,311 | B2 * | 7/2009 | Umemoto | 177/25.16 |
| 2002/0134589 | A1 * | 9/2002 | Montagnino et al. | 177/25.16 |
| 2005/0209528 | A1 | 9/2005 | Sato et al. | |
| 2006/0006005 | A1 * | 1/2006 | Dumornay et al. | 177/25.13 |

(Continued)

FOREIGN PATENT DOCUMENTS

CN 1669523 A 9/2005

(Continued)

OTHER PUBLICATIONS

"Iphone: User's Guide", downloaded Oct. 6, 2010, p. 89 (http://manuals.info.apple.com/en/iphone_user_guide.pdf).*

(Continued)

Primary Examiner — Randy W Gibson
(74) Attorney, Agent, or Firm — Buchanan Ingersoll & Rooney PC

(57) ABSTRACT

When a human subject presses a start switch S and stands on a platform (10) of a measurement apparatus (100), the weight of the human subject is measured, and the measurement result is stored as measurement data xi (i is a natural number) in a rewritable memory (150c). When the start switch S and a difference key F are pressed, measurement data xi stored in rewritable memory (150c) is read so as to be displayed temporarily on a display unit (120). Display unit (120) changes to a zero display, "0.00 kg", and when the human subject stands on platform (10), the current weight of the human subject is measured. A CPU (110) uses a calculation equation read from a ROM (150b) to execute a difference output process in which the difference between the measurement data showing the current weight and measurement data xi read from rewritable memory (150c) is output.

2 Claims, 13 Drawing Sheets

U.S. PATENT DOCUMENTS

2008/0281222 A1* 11/2008 Fukada ............... 600/547
2010/0130831 A1* 5/2010 Sato et al. ............. 600/300

FOREIGN PATENT DOCUMENTS

| EP | 0 359 243 A2 | 3/1990 |
|---|---|---|
| EP | 1 262 745 A1 | 12/2002 |
| JP | 2005-106552 A | 4/2005 |
| WO | WO 90/07101 A1 | 6/1990 |

OTHER PUBLICATIONS

Chinese Office Action issued Mar. 11, 2010 by the Chinese Patent Office in Chinese Patent Application No. 200810213331.8 and English language translation of Chinese Office Action.

Extended European Search Report issued May 7, 2010 by the European Patent Office in European Patent Application No. 08 16 0133.

* cited by examiner

MEASUREMENT APPARATUS FOR MEASURING CHANGES IN BODY COMPOSITION

BACKGROUND OF THE INVENTION

1. Field of the Invention

The present invention relates to a measurement apparatus that has a difference output function for outputting the difference between two measurement results.

2. Description of Related Art

There is disclosed, in Japanese Patent Application Laid-Open Publication No. 2005-106552, a weight scale for weighing a baby. To weigh a baby with this scale, a measurement is taken first of the mother alone, and a second measurement is taken of the mother with the baby, and the difference in weight between the first and the second measurements is output as the baby's weight. This is called a tare weight output function (i.e., difference output function). This weight scale having the tare weight output function holds the data showing the result of the first measurement for a predetermined time period, and only in a case in which the subsequent measurement is taken within the predetermined time period, is the difference in weight between the first and the subsequent measurements obtained and displayed.

However, with the above weight scale having the difference output function, the second measurement must be taken within the predetermined time period. Because it is not allowed to take the second measurement at a time later than the predetermined time period, the time at which the second measurement is taken cannot be freely selected. As a result, the applications of the difference output function are limited, and therefore, a user cannot freely use the difference output function in a way the user wishes.

SUMMARY OF THE INVENTION

The present invention was made in consideration of the above, and the present invention has as an object to provide a measurement apparatus that allows a user to freely use the difference output function without limiting the applications of the function.

In one aspect (a first aspect), the present invention provides a measurement apparatus having a measurer that measures an index relating to body compositions of a human subject; a difference output instructor that instructs the measurement apparatus to output the difference between a previous measurement result and a current measurement result, the previous measurement result measured by the measurer being a base value and the current measurement result measured by the measurer being a comparison value; a memory storage device that stores a measurement result of the measurer; and a difference outputter that, in a case in which the measurement apparatus is instructed to output the difference by the difference output instructor, reads, from the memory storage device, the stored measurement result as the base value and that calculates the difference between the base value and the comparison value. An index relating to body compositions of humans includes weight, ratio of body fat, amount of visceral fat (visceral fat area, ratio of visceral fat), body water mass, extracellular fluid volume, intracellular fluid volume, body fat mass, lean body mass, muscle mass, bone mass, basal metabolic rate, and the like. In the invention, the user of the apparatus may be the human subject who is to be measured. Alternatively, the user may be an operator of the measurement apparatus who assists the human subject to operate the apparatus.

According to the present invention, because there are provided a memory storage device that stores a measurement result and a difference output instructor (for example, a difference key F in the first to fourth embodiments) that instructs the measurement apparatus to output the difference between a previous measurement result and a current measurement result, the difference can be output simply by instructing the output of the difference and without having to perform the measurement of the comparison value (the current measurement) within a predetermined time period, since the measurement of the base value (the previous measurement) was performed. Therefore, a user is allowed to freely use the difference output function of the measurement apparatus for a desired purpose, i.e., the degree of freedom in applications of the difference output function is enhanced. An example of the present invention is shown in the first embodiment.

In the memory storage device, the data stored is preferably updated (overwritten with the newly measurement result) every time a measurement is performed. Alternatively, the memory storage device may preferably be provided with memory areas for storing plural data sets of measurement results, in which case the difference outputter may preferably read the immediately previous measurement result as the base value. Furthermore, a measurement result at the time when the measurement apparatus is instructed to output the difference by the difference output instructor (i.e., the current measurement result or the comparison value) may or may not be stored in the memory storage device, and the present invention is not limited to either. In a case in which the current measurement result is stored, the stored current measurement result may be used as the base value at a later time for a case in which the output of the difference is instructed, or the stored current measurement result may be simply stored as history data.

The difference outputter includes a difference calculator that calculates the difference by calculation, and a difference outputter that outputs the difference obtained by the difference calculator. "Outputting the difference" includes displaying an image showing the value showing the difference on a display of the measurement apparatus, outputting the value showing the difference by speaking in if the apparatus has an audio outputting function, and printing out an image showing the value showing the difference if the apparatus has a printing function. Furthermore, outputting the difference includes, in a case in which the measurement apparatus has a terminal for connecting to an external device, outputting the difference data showing the value of the difference to an external device.

In another aspect, the present invention provides a measurement apparatus, comprising: a weigher that measures the weight of a subject; a difference output instructor that instructs the measurement apparatus to output a difference between a previous measurement result and a current measurement result, the previous measurement result measured by the weigher being a base value, and the current measurement result measured by the weigher being a comparison value; a memory storage device that stores a measurement result of the weigher; and a difference outputter that, in a case in which the measurement apparatus is instructed to output the difference by the difference output instructor, reads, from the memory storage device, the stored measurement result as the base value and that calculates the difference between the base value and the comparison value. In the present invention, a subject to be measured is not limited to a human subject. Accordingly, the difference to be output need not indicate a change in the value of a certain index of a human subject between the previous and the current measurements. For example, in a case in which a user (or a human subject) first stands on a platform of a measurement apparatus alone and then stands on the platform holding a piece of luggage, the user can obtain the difference between the first measurement result (previous measurement result) and the second measurement result (current measurement result), the difference indicating the weight of the luggage. According to this second aspect of the present invention, the same effects as in the above first aspect are attainable.

In a preferred embodiment of the present invention, the measurement apparatus may be further provided with a storage instructor (for example, a memory key M in the second and fourth embodiments) that instructs the measurement apparatus to store in the memory storage device a measurement result measured by the measurer as the base value, and the memory storage device may store a measurement result measured by the measurer only in a case in which the measurement apparatus is instructed by the storage instructor to store a measurement result measured by the measurer. According to this embodiment, only the measurement result specified by the storage instructor is stored in the memory storage device, and in a case in which the measurement apparatus is instructed to output the difference by the difference output instructor at the time of a later measurement, a measurement result as of the desired previous timing is used as the base value for the calculation of the difference. In other words, the base value can be fixed no matter how many times measurements are performed from the measurement of the base value up to the measurement of the comparison value. Thus, a user or a human subject can freely select (or specify) the base value based on which the difference is obtained, and the degree of freedom in application of the difference output function is further enhanced. An example of the present invention is shown in the second embodiment.

In another preferred embodiment of the present invention, the measurement apparatus may be further provided with an identifier (for example, an individual key P in the third and fourth embodiments) that uniquely identifies each of plural human subjects by identification information, the memory storage device may store, in a case in which one of the plural human subjects is specified by the identification information, a measurement result of the measurer in association with the identification information; and, in a case in which the measurement apparatus is instructed to output the difference by the difference output instructor and in a case in which one of the plural human subjects is specified by the identifier, the difference outputter may read from the memory storage device the base value that has been stored in association with the specified identification information to output the difference between the base value and the comparison value. An example of the present invention is shown in the third embodiment.

According to the present embodiment, the base value to be compared can be selected without fail even in a case in which plural human subjects use the measurement apparatus. Specifically, because the apparatus is provided with an identifier that uniquely identifies each of the plural human subjects by identification information, even in a case in which, after a human subject (human subject A) has a first measurement taken, and another human subject (human subject B) uses the same measurement apparatus before the human subject A has a second measurement taken, a situation in which the difference between the measurement result of the human subject A and that of the human subject B is erroneously obtained is prevented from occurring. Therefore, for example, in a place such as a gym or a health club where a number of human subjects (users) use a single measurement apparatus, a user can obtain the difference as the effect of the subject's exercise without fail.

In still another preferred embodiment of the present invention, the measurement apparatus may be further provided with a storage instructor (for example, a memory key M in the fourth embodiment) that instructs the measurement apparatus to store in the memory storage device a measurement result measured by the measurer as the base value, and only in a case in which the measurement apparatus is instructed by the storage instructor to store a measurement result measured by the measurer and in a case in which one of the plural human subjects is specified by the identifier, the memory storage device may store the measurement result in association with the specified identification information. According to the present embodiment, a human subject is allowed to specify, from among previous measurement results of the human subject, a measurement result that was measured at a desired timing as the base value, based on which the difference is obtained. Therefore, when compared with a case in which no storage instructor is provided, the degree of freedom in the applications of the difference output function is further enhanced. An example of the present invention is shown in the fourth embodiment.

Furthermore, the difference outputter may preferably include a displayer that displays the difference on the display unit, and the displayer may preferably display the difference in a first scale interval in a case in which the difference falls within the predetermined range, whereas the displayer displays the difference in a second scale interval that is larger the first scale interval in a case in which the difference is outside of the predetermined range. According to the present embodiment, because the first scale interval is used in a case in which a small difference is displayed, a human subject is able to be made aware of a small amount of change, for example, in weight before and after exercise or bathing, urination, breastfeeding, or the like with a smaller scale interval.

BRIEF DESCRIPTION OF THE DRAWINGS

With reference to the accompanying drawings, various embodiments of the present invention will be described hereinafter. In the drawings.

DETAILED DESCRIPTION OF PREFERRED EMBODIMENTS

A: First Embodiment

In the following, description will be given of a first embodiment of the present invention with reference to the attached drawings.

Figure 1:
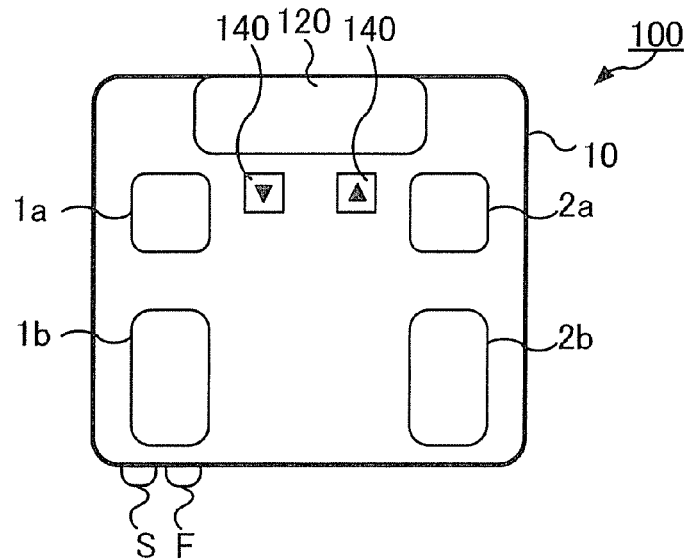
FIG. 1 is a plane view of a measurement apparatus 100 according to the first embodiment of the present invention.

FIG. 1 is a plane view showing a measurement apparatus 100 according to the present embodiment. Measurement apparatus 100 according to the present embodiment is a weight scale having a difference output function. The difference output function is a function to calculate and output the difference between a current measurement result and an earlier (or previous) measurement result. The difference output function can be used, for example, for a case in which a measurement of the weight of a human subject is taken before exercise (i.e., a previous measurement), another measurement of the same subject is taken after exercise (i.e., a current measurement), and subsequently, the difference between the previous and current measurement results is calculated for output. In this case, increase or decrease in body weight before and after exercise is output, whereby the effect of the exercise can be determined. The following description will be given of a case in which the difference output function is used for the above example.

As shown in FIG. 1, measurement apparatus 100 is provided with a platform 10 for a human subject to stand on, a start switch S for turning on measurement apparatus 100, and a difference key F. Start switch S is a foot switch that is turned on when a button is pressed by the foot of a human subject or a user. Measurement apparatus 100 is turned on when the button of start switch S is pressed and subsequently measures a body weight of the human subject who is standing on platform 10. A result of the measurement is displayed on display unit 120 and is stored in a rewritable memory 150c (described below) as measurement data xi, in which "i" is a natural number. In a case in which a predetermined time has elapsed with no operations or measurements being performed since start switch S was pressed, measurement apparatus 100 is automatically turned off. In the present embodiment, the user of the apparatus is the same as the human subject to be measured. Alternatively, however, a user may be an operator of the measurement apparatus who assists the human subject in the operation of the apparatus.

In a case in which, after start switch S is pressed, difference key F is pressed, and then the weight is measured, measurement apparatus 100 reads measurement data xi stored in rewritable memory 150c as a base value and calculates the difference between the current weight and the base value. Difference key F thus serves as a difference output instruction means or a difference output instructor that instructs the measurement apparatus to output a difference between a previous measurement result (base value) and a current measurement result (comparison value).

Figure 2:
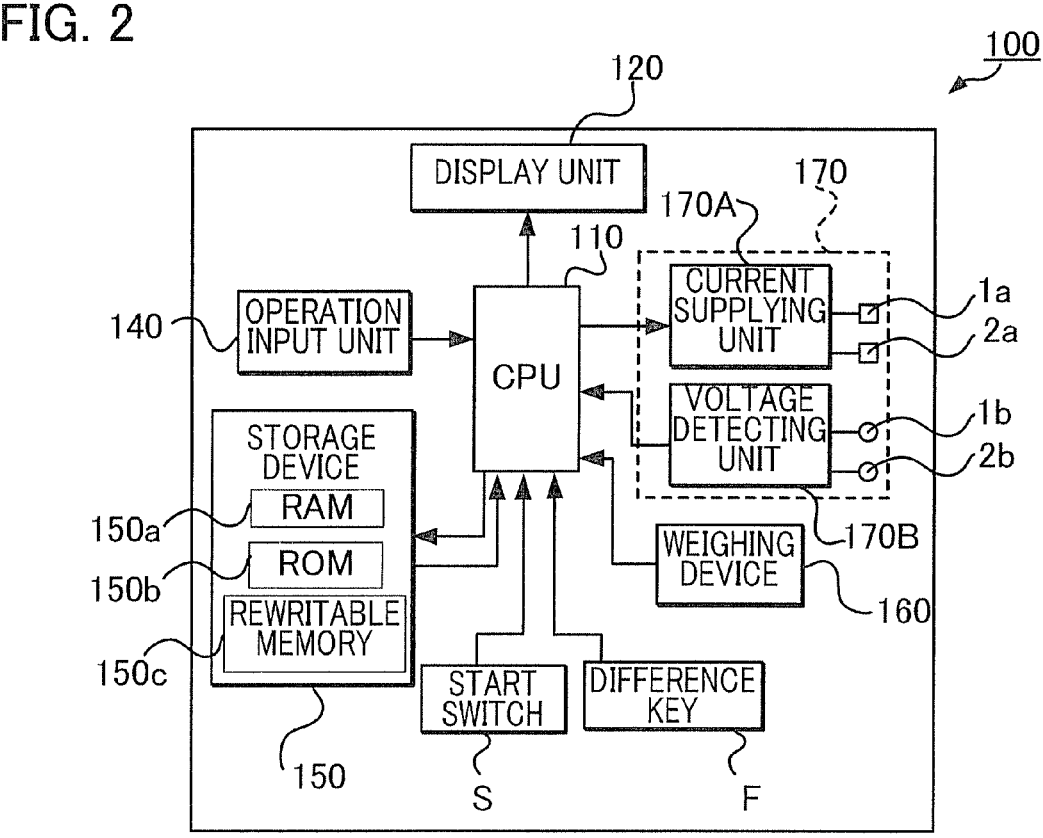
FIG. 2 is a block diagram showing an electrical configuration of measurement apparatus 100.

FIG. 2 is a block diagram showing an electrical configuration of measurement apparatus 100. As shown in FIGS. 1 and 2, measurement apparatus 100 has, on the top surface of platform 10, current supply electrodes 1a and 2a, voltage detection electrodes 1b and 2b, a display unit 120 for displaying operation guidance messages for a human subject or a user, as well as indications of measurement results, and an operation input device 140 through which a human subject or a user inputs various instructions. Display unit 120 is a display device such as an LCD (Liquid Crystal Display). Operation input device 140 is provided with an Up-Key and a Down-Key. A human subject or a user operates at least one of the Up-Key and the Down-Key in accordance with guidance messages displayed on display unit 120, thereby inputting various instructions. Display unit 120 may be provided with a touch panel function, so that display unit 120 can also serve as an operation input device.

There are provided inside platform 10 a memory storage device 150, a weighing device 160, a bioelectrical impedance device 170, and a CPU (Central Processing Unit) 110. Weighing device 160 is provided with a weight sensor (not shown). The weight sensor is capable of outputting a weight of a human subject, when the human subject stands on platform 10, as weight data. The weight sensor is, for example, a load cell having an elastic body and strain gauges fitted thereto, and the load cell detects and outputs changes in voltage caused by strains of the strain gauges. The weight data output from weighing device 160 is digitalized by an A/D converter (not shown) to be supplied to CPU 110. CPU 110, upon receiving the weight data from weighing device 160 through the A/D converter, stores the weight data as measurement data xi in rewritable memory 150c.

Weighing device 160 (measurer) has a high resolution power, for example, of $10^{-3}$ (0.001 kg), the measurement data xi thus being represented in a unit of 1 g. In a case in which the above difference output function is not used, i.e., in a case in which a weight measurement is simply taken, CPU 110 causes a result of the measurement to be displayed in a scale interval that is coarser than the resolution power. In this embodiment, the result of the measurement is displayed in the scale interval of 100 g (i.e., 0.1 kg, hereinafter referred to as a "normal display scale" (second display scale)), although this is not limited thereto. Therefore, in a case in which the measurement data xi is 58.435 kg, it is displayed as 58.4 kg in the normal display scale.

On the other hand, in a case in which a measurement is performed using the difference output function, if the difference βp (p is a natural number) is within the range of, for example, ±20 kg, the difference will be displayed at a scale interval of 20 g (hereinafter referred to as a "fine display scale" (first display scale)). Thus, the calculated difference values displayed in the fine display scale are discrete values with 20 g difference. Given that "m" is the displayed value and "n" is the difference value, the difference value n will be displayed as the displayed value m so as to satisfy the expression m−10≦n<m+10. In other words, the difference value n is rounded to the displayed value in at a scale interval of 20 g. Therefore, for example, in a case in which the difference βp is −2.726, it will be displayed as −2.72 kg. Conversely, in a case in which the difference βp does not fall in the range of ±20 kg, the difference value will be displayed in the normal display scale, and therefore, the difference value n is rounded to the first decimal place to be the displayed value m. For example, the difference βp 23.235 kg will be displayed as 23.2 kg.

Bioelectrical impedance device 170 has a current supplying unit 170A and a voltage detecting unit 170B. Current supplying unit 170A, when a human subject stands on platform 10, applies high-frequency constant microcurrent to the sole of each foot of the human subject through current supply electrodes 1a and 2a that have been formed on platform 10. Voltage detecting unit 170B measures a potential difference between voltage detection electrodes 1b and 2b. The data of the potential difference is digitalized by the A/D converter (not shown) to be supplied as bioelectrical impedance Z to CPU 110.

Memory storage device 150 has a RAM (Random Access Memory) 150a, a ROM (Read Only Memory) 150b, and rewritable memory 150c. ROM 150b is a non-volatile memory and has stored various computer programs or computer program elements for causing CPU 110 to execute various processes, as well as a computer program or a computer program element for causing CPU 110 to execute an operation according to the present embodiment. Furthermore, there are stored in ROM 150b a calculation equation for obtaining the difference between a previous measurement result (base value) and a current measurement result (comparison value) of weight measured by weighing device 160. Specifically, the calculation equation is expressed as the difference βp=comparison value—base value. CPU 110 executes computation in accordance with the calculation equation, thereby serving as a difference output means (difference outputter) for obtaining the difference between a previous measurement result and a current measurement result.

RAM 150a is used as a work area by CPU 110. CPU 110 temporarily stores, in RAM 150a, weight data supplied from weighing device 160 and measurement data xi read from rewritable memory 150c, to be used as parameters later for calculation.

Rewritable memory 150c is for example an EEPROM (Electronically Erasable and Programmable Read Only Memory), and measurement data xi is updated (overwritten with the latest measurement result) every time a measurement is performed by weighing device 160.

CPU 110 operates according to the computer program or the computer program element stored ROM 150b and controls display unit 120 and memory storage device 150. Furthermore, CPU 110 executes an operation in accordance with signals received from operation input device 140, start switch S, and difference key F. For example, CPU 110 executes a difference output process according to the present embodiment in a case in which difference key F is pressed.

Figure 3:
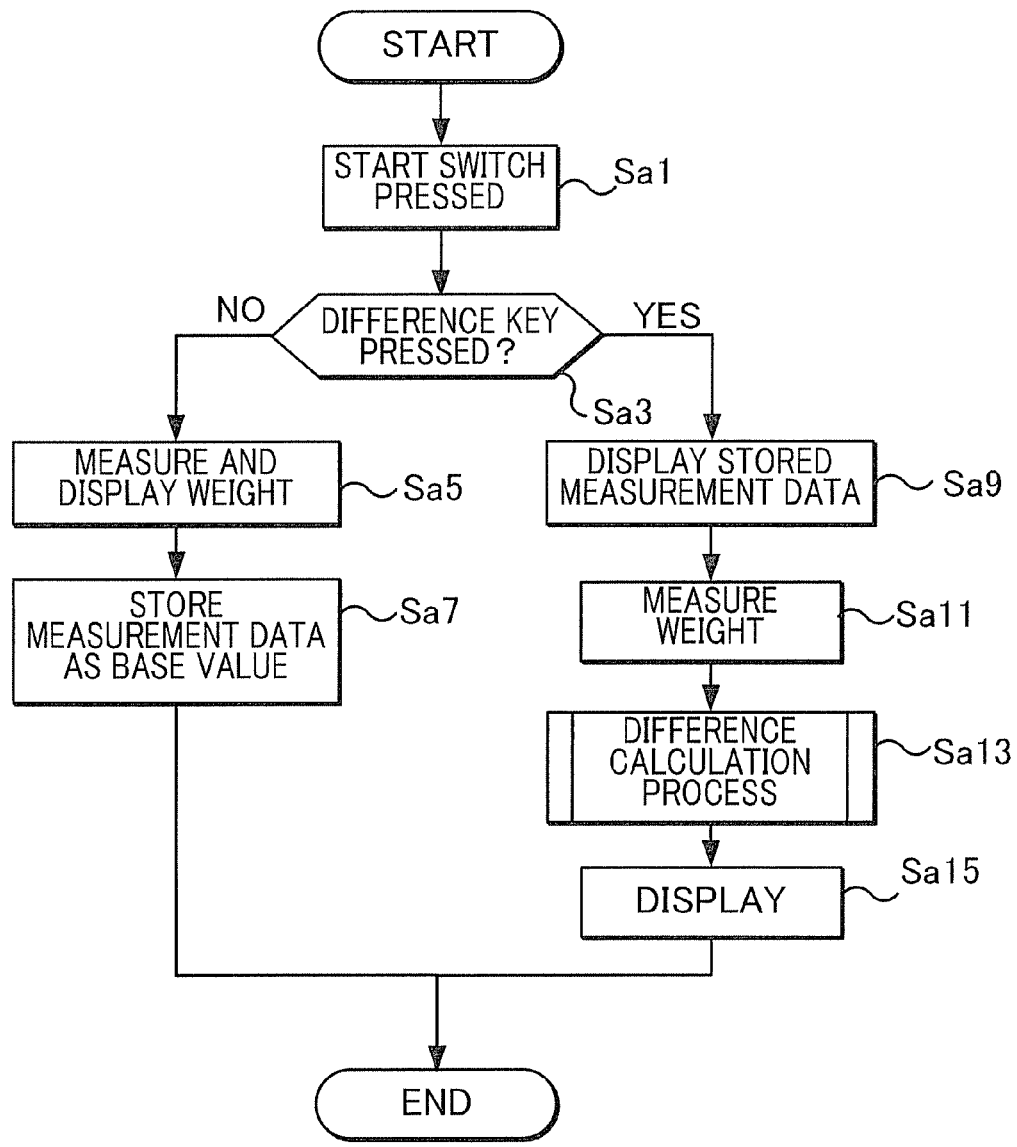
FIG. 3 is a flowchart showing a flow of operation according to the present embodiment.

FIG. 3 is a flowchart showing a flow of operation according to the present embodiment.

As shown in FIG. 3, in Step Sa1, in a case in which start switch S is pressed, measurement apparatus 100 is turned on. CPU 110 first displays an initial screen, "0.00 kg" (i.e., zero display), on display unit 120. CPU 110 then determines whether difference key F has been pressed (Step Sa3). In a case in which a result of this determination is negative, i.e., in a case in which a human subject stands on platform 10 without pressing difference key F, the process proceeds to Step Sa5, CPU 110 displays a measured weight of the human subject on display unit 120. CPU 110 then stores the measurement result (measurement data xi) as a base value in rewritable memory 150c (Step Sa7), and the process is then finished.

On the other hand, in a case in which difference key F is pressed, it is determined to be YES in Step Sa3, and in Step Sa9, CPU 110 reads the measurement data xi (base value) stored in rewritable memory 150c and temporarily displays the data on display unit 120. The display then returns to the zero display. If the human subject then stands on platform 10, a weight of the human subject is measured (Step Sa11), and weight data showing the measured weight is temporarily stored in RAM 150a. Subsequently, CPU 110 reads from ROM 150b the calculation equation to execute the difference calculation process (Step Sa13). The measurement data xi indicating the current weight may be displayed before the difference calculation process is executed.

Figure 4:
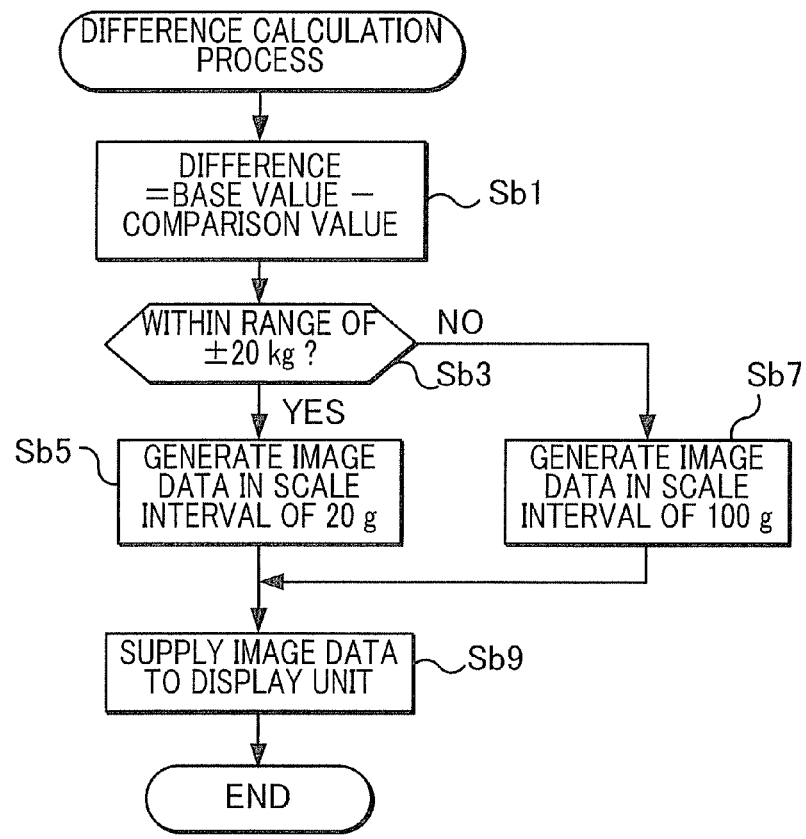
FIG. 4 is a flowchart showing detailed flow of a difference calculation process shown in FIG. 3.

FIG. 4 is a flowchart showing details of the flow of the difference calculation process shown in FIG. 3. In Step Sb1, CPU 110 assigns into the calculation equation the measurement result (the current measurement result, i.e., comparison value) read from RAM 150a and the measurement data xi (the base value) read from rewritable memory 150c, to obtain the difference βp therebetween. The difference βp obtained at this time indicates the increased or decreased amount of the comparison value in reference to the base value. Specifically, the difference βp will be a negative value in a case in which the current measurement result is smaller than the base value measured previously, whereas the difference βp will be a positive value in a case in which the current measurement result is larger than the base value measured previously.

Subsequently in Step Sb3, CPU 110 determines whether the difference βp is within the range of ±20 kg. In a case in which a result of the determination is affirmative, CPU 110 generates image data showing the difference βp in the fine display scale, i.e., at the scale interval of 20 g (Step Sb5) and supplies the image data to display unit 120 (Step Sb9). On the other hand, in a case in which a result of the determination of Step Sb3 is negative, i.e., the difference βp is not within the range of ±20 kg, CPU 110 generates image data showing the difference βp in the normal display scale that is coarser than the fine display scale, i.e., at the scale interval of 100 g (Step Sb7) and supplies the image data to display unit 120 (Step Sb9). CPU 110 then ends the difference calculation process, and the routine returns to Step Sa15 of FIG. 3.

In Step Sa15, an image showing the difference βp is displayed on display unit 120 of measurement apparatus 100. CPU 110 will continue to display the image for a predetermined time period, to end the process. In a case in which no operations are performed at measurement apparatus 100 for a predetermined time period thereafter, CPU 110 turns off measurement apparatus 100. Measurement apparatus 100 will stay in the off state until start switch S is again pressed.

Various applications of this difference output function can be conceived. For example, the body weight of a baby can be obtained if the mother first stands on a weight scale alone and then again stands on the scale holding the baby. Another example is a person on a diet who measures body weight before and after exercise so that the effect of the exercise is shown in actual weight values. In the former case, the mother will probably have a measurement taken of herself holding the baby in a relatively short time (e.g., a few minutes) after having the first measurement of herself alone. However, in the latter case, the length of time between the first measurement before exercise and the second measurement after exercise depends on the time required for the exercise and could be hours, days, or even months. Thus, the lengths of time between the previous measurement and the current measurement are all different. Therefore, in the present embodiment, difference key F is provided so that the difference between the previous and the current measurement results can be taken regardless of the length of time between the two measurement time points. According to the embodiment, a human subject simply presses difference key F to cause the previous measurement result to be read from the memory, and the difference between the current measurement result and the read previous measurement result is then obtained. Thus, there is no temporal restriction in that the measurement of the comparison value need not be performed within a prescribed time period, and therefore, a human subject can freely use the difference output function for a purpose the human subject desires. Conversely, in the conventional method in which the previous measurement result is stored only for a predetermined time period, the measurement of the comparison value must be taken within the predetermined time period, and therefore the difference output function can be used only for a limited purpose. Thus, with the difference output function of measurement apparatus 100 according to the present embodiment, the applications of the difference output function will be dramatically increased.

Furthermore, the scale interval of the displayed difference data is switched to the normal display scale or to the fine display scale depending on whether the difference data is within the predetermined range (within the range of ±20 kg in the present embodiment). Therefore, the difference can be displayed in the scale interval that is suited for the quantity of the difference. In a case in which a user wishes to determine a small amount of change as the difference in particular, the increase or decrease can be accurately obtained.

In the present embodiment, a description has been given of a case in which the obtained difference is output by displaying an image showing the difference βp on display unit 120. Alternatively, difference data showing the difference βp may be transmitted to an external device such as a personal computer connected to measurement apparatus 100. In this case, the determination is not performed as to whether the difference is within the range of ±20 kg, but the difference data itself is output to an external device.

Furthermore, in the above description, the difference calculation process is executed if difference key F is pressed after start switch S has been pressed, but this is not limited thereto. The difference computation function may be executed even when only difference key F is pressed. More specifically, in a case in which the power of measurement apparatus 100 is in an ON state, the difference calculation process may be executed only with difference key F. In a case in which the power is in an OFF state, difference key F may cause measurement apparatus 100 to be turned on and also to execute the difference calculation process.

Figure 5:
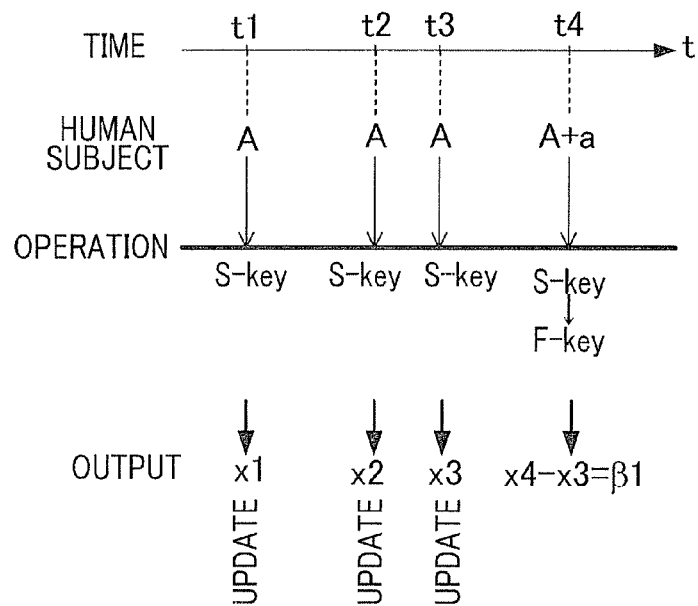
FIG. 5 is a time chart for describing how a measurement process of the present embodiment is performed.

FIG. 5 is a time chart showing a measurement process in a case in which a human subject A uses measurement apparatus 100. As shown in FIG. 5, human subject A presses start switch S ("S-key" shown in the figure), stands on platform 10, and has a measurement taken at Time t1. The measurement data x1 measured at this time is stored in rewritable memory 150c. Subsequently, at Times t2 and t3 each, human subject A again has another measurement taken. The measurement data x2 and x3 measured at each Time t2, t3 is stored in rewritable memory 150c in an updated manner. Specifically, at Time t2, measurement data x1 is overwritten with measurement data x2; and at Time t3, measurement data x2 is overwritten with measurement data x3.

Subsequently at Time t4, human subject A first presses start switch S and then presses difference key F ("F-key" shown in FIG. 5), data stored in rewritable memory 150c, i.e., measurement data x3 is displayed on display unit 120. The display then turns to the zero display, "0.00 kg". Human subject A then stands on platform 10 of measurement apparatus 100, and a measurement of the current weight is taken (measurement data x4). Subsequently, the above difference calculation process is executed. Specifically, the calculation equation is used to obtain the difference β1=x4−x3, and a result of the calculation is displayed on display unit 120. Given that x4=58.452 kg and x3=59.235 kg, the difference will be β1=58.452−59.235=−0.783 kg. Therefore, the difference data will be displayed as "−0.78 kg" in the scale interval of 20 g on display unit 120. Human subject A will then find that the weight has been reduced by 0.78 kg from Time t3 to Time t4.

As described in the foregoing, in the present embodiment, in a case in which a measurement is taken without difference key F being pressed, a measurement result is updated every time the measurement is performed, whereas a measurement is taken after difference key F has been pressed, a measurement result that is being stored at a time when difference key F is pressed (i.e., the immediately previous measurement result) is read, so that the difference between the read measurement result and the current measurement result is obtained. Therefore, the measurement performed at Time t4 of FIG. 5 need not be performed within a predetermined time period since Time t3, and a user can have the measurement of Time t4 taken at a desired timing. Therefore, according to the present embodiment, the applications of the difference output function will be increased, and the difference output function will be more useful to users.

B: Second Embodiment

Description will next be given of a second embodiment of the present invention, with reference to FIGS. 6 to 9.

The present embodiment differs from the above first embodiment in that a measurement apparatus is provided with a memory key in addition to start switch S and difference key F, the memory key for instructing measurement apparatus 100 to store the base value.

It should be noted that in each of the drawings, FIGS. 6 to 9, the same reference numerals are used for the same components as in the first embodiment, and the descriptions thereof will be omitted as appropriate.

Figure 6:
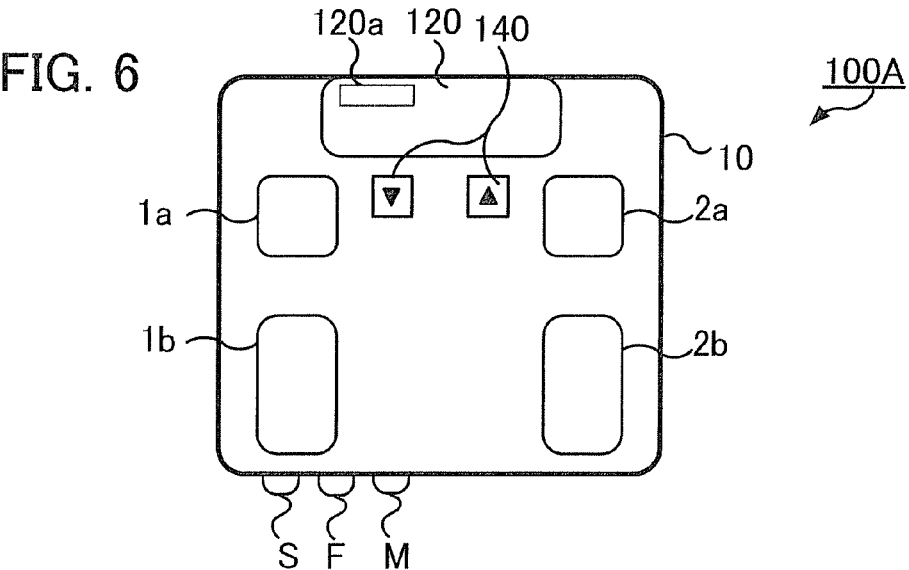
FIG. 6 is a plane view showing a measurement apparatus 100A according to a second embodiment of the present invention.
Figure 7:
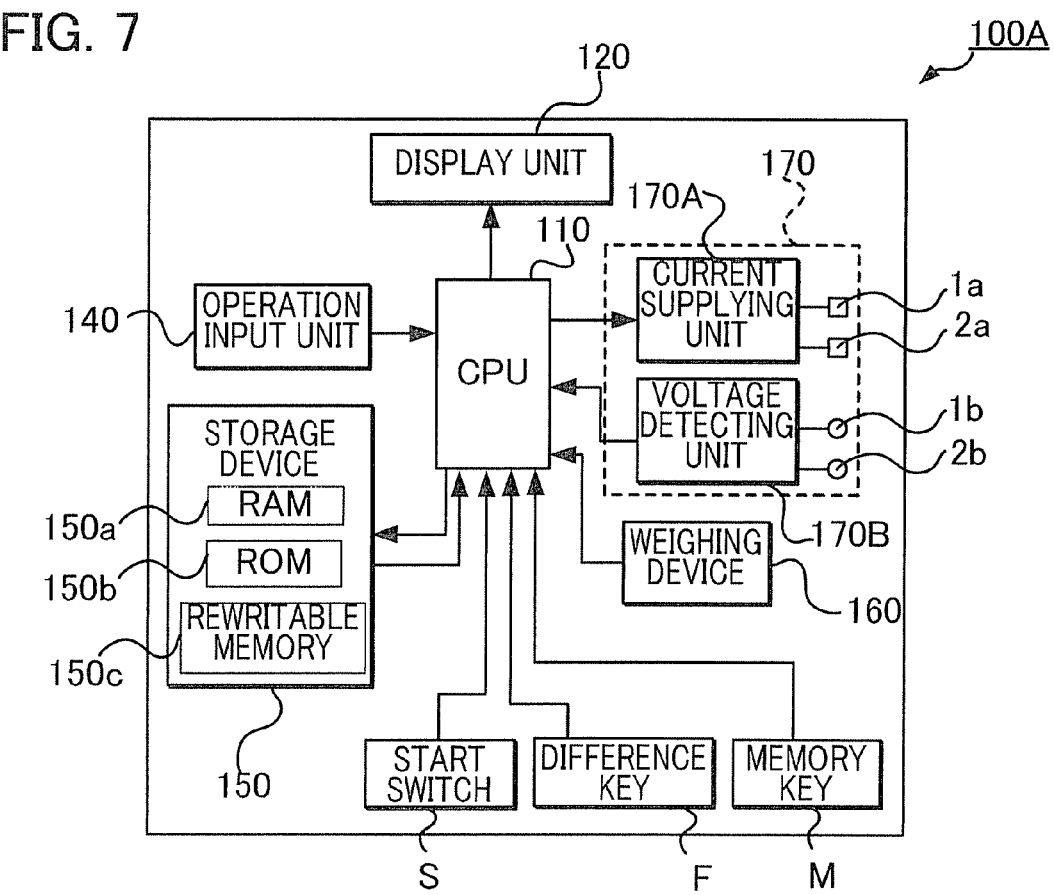
FIG. 7 is a block diagram showing an electrical configuration of measurement apparatus 100A.
Figure 9:
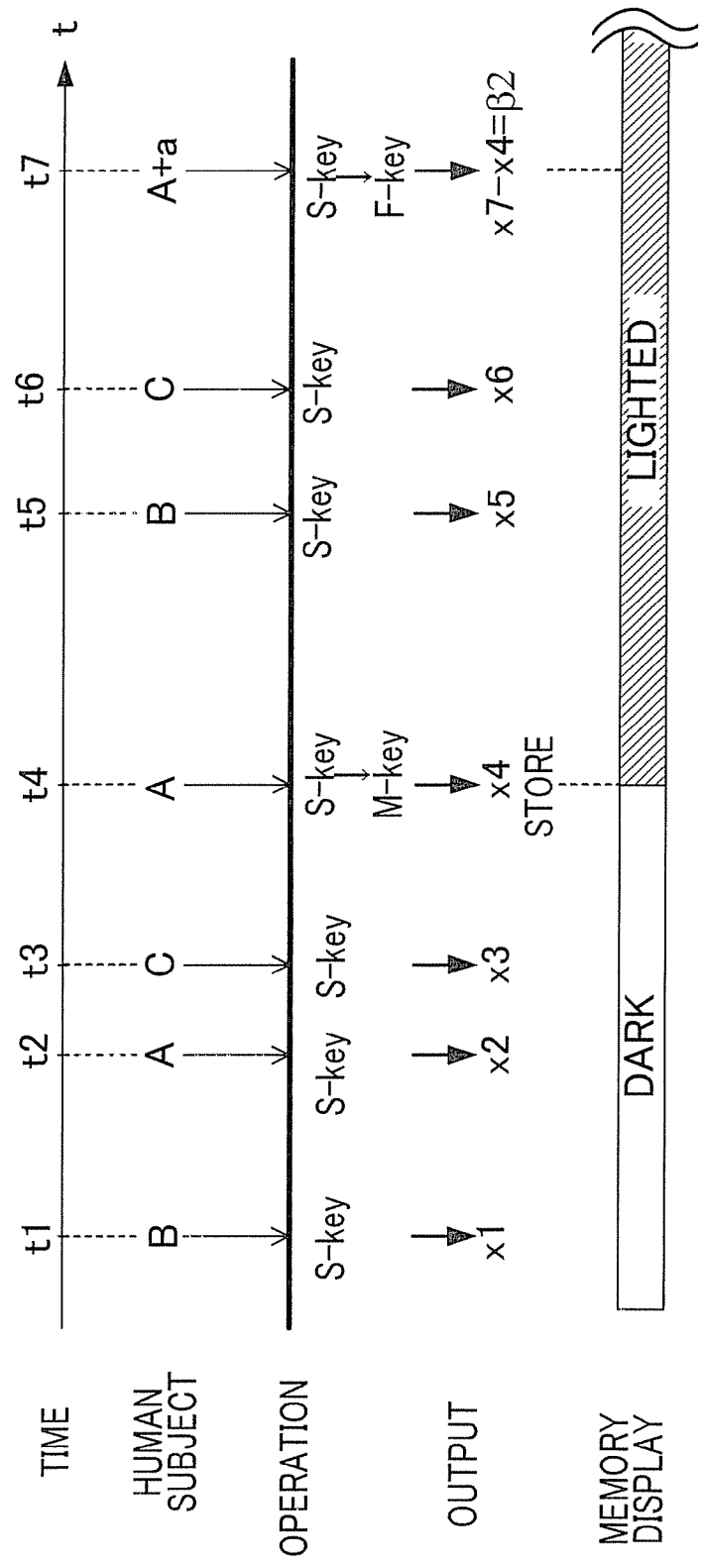
FIG. 9 is a time chart for describing how a measurement process of the present embodiment is performed.

FIG. 6 is a plane view showing a measurement apparatus 100A according to the second embodiment of the present invention. FIG. 7 is a block diagram showing an electrical configuration of measurement apparatus 100A. Furthermore, FIG. 9 is a time chart for describing how measurements are taken at measurement apparatus 100A.

As shown in FIGS. 6 and 7, measurement apparatus 100A is provided with a memory key M in addition to start switch S and difference key F. In a case in which a weight is measured after memory key M is pressed, measurement data xi showing the measurement result is stored in rewritable memory 150c. In other words, only the measurement data xi showing a weight that is measured when memory key M is pressed is stored in rewritable memory 150c. Specifically, as shown in FIG. 9, measurements were taken at Times t1, t2, t3, t4, t5, and t6, but the only measurement data x4 was stored in rewritable memory 150c because memory key M ("M-key" shown in the figure) was pressed at Time t4. Thus, memory key M serves as a storage instructor (storage instruction means) that instructs measurement apparatus 100A that a particular measurement data xi be stored as the base value in rewritable memory 150c.

Furthermore, as shown in FIG. 6, display unit 120 is provided with a memory display area 120a. As shown in FIG. 9, memory display area 120a lights up when memory key M is pressed, thereby indicating that rewritable memory 150c is holding measurement data xi. Memory display area 120a turns dark when measurement data xi is deleted. Measurement data xi is deleted, for example, by pressing memory key M when the power is off or by providing a memory reset key (not shown) that is different from memory key M.

Figure 8:
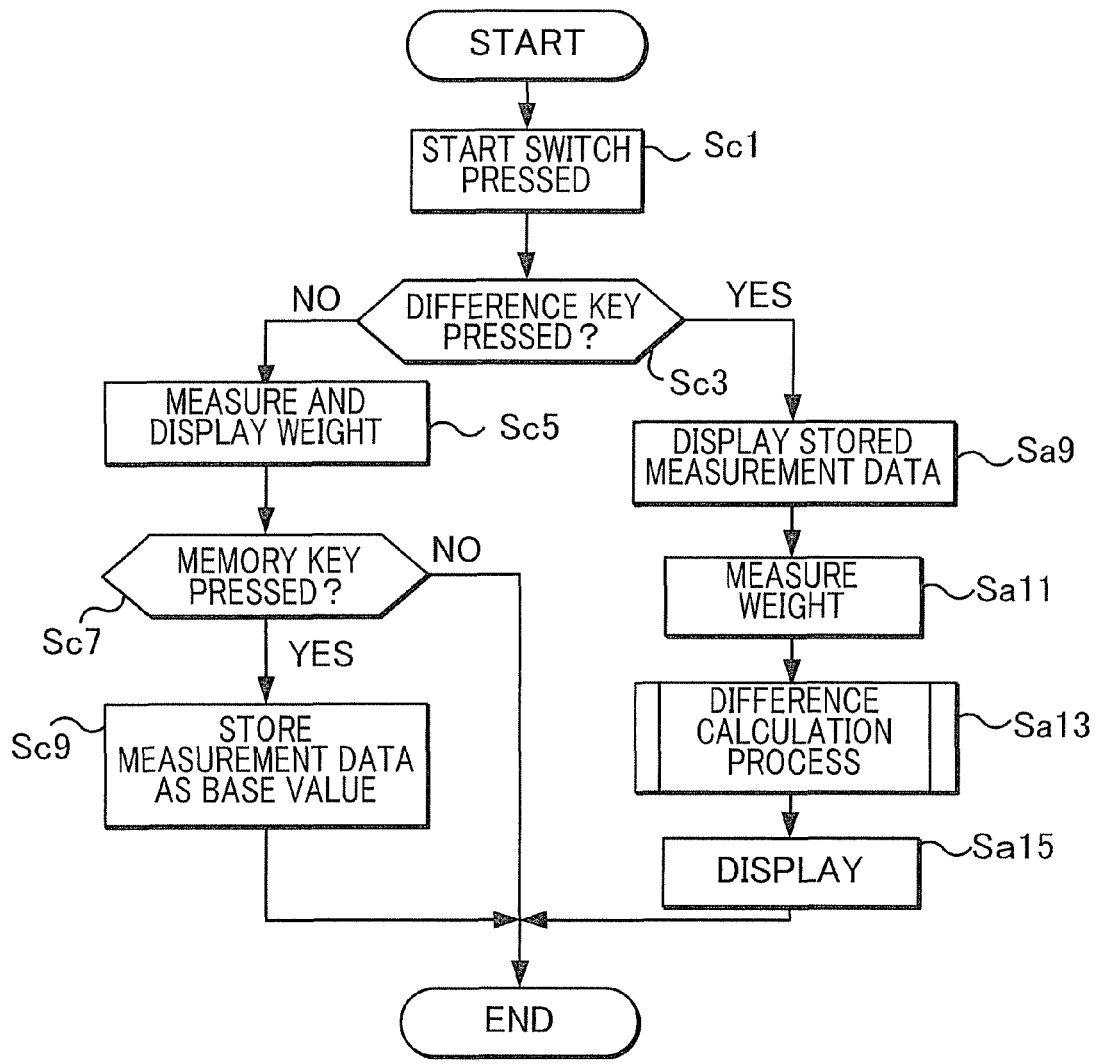
FIG. 8 is a flowchart showing a flow of operation according to the present embodiment.

FIG. 8 is a flowchart showing a flow of operation of the present embodiment. As shown in FIG. 8, in Step Sc1, in a case in which start switch S is pressed, measurement apparatus 100A is turned on. CPU 110 then determines whether difference key F is pressed (Step Sc3). In a case in which a result of the determination is negative, if a human subject stands on platform 10, the weight of the human subject is measured, and the result of the measurement is displayed on display unit 120 (Step Sc5). Subsequently, CPU 110 determines whether memory key M is pressed (Step Sc7). In a case in which a result of the determination is negative, i.e., memory key M is not pressed, CPU 110 ends the measurement process.

On the other hand, in a case in which a result of the determination of Step Sc7 is affirmative, i.e., memory key M is pressed, CPU 110 stores measurement data xi in rewritable memory 150c and lights up memory display area 120a, and then the measurement process is completed.

On the other hand, in a case in which a result of the determination of Step Sc3 is affirmative, i.e., difference key F is pressed, CPU 110 reads measurement data xi that has been stored in rewritable memory 150c for temporal display on display unit 120 (Step Sa9), and the display will then change to the zero display "0.00 kg". When a human subject stands on platform 10, a measurement is taken of the weight of the human subject (Step Sa11), and CPU 110 then executes the difference calculation process (FIG. 5) (Step Sa13). Subsequently, in Step Sa15, CPU 110 displays an image showing the difference βp and ends the measurement process.

FIG. 9 is next referred to, to describe a measurement process performed at measurement apparatus 100A. In this example, it is assumed that no measurement data xi is stored in rewritable memory 150c at Time t1. Therefore, memory display area 120a is dark at Time t1.

As shown in FIG. 9, at Time t1, a human subject B presses start switch S and stands on platform 10, but human subject B does not press memory key M after the measurement. As a result, CPU 110 ends the measurement process without storing measurement data x1. At Time t2, a human subject A presses start switch S and stands on platform 10, but human subject A does not press memory key M. Therefore, CPU 110 ends the measurement process without storing measurement data x2. Subsequently at Time t3, a human subject C presses start switch S and stands on platform 10, but human subject C does not press memory key M in the same way as was done at Times t1 and t2. Therefore, CPU 110 ends the measurement process without storing measurement data x3.

At Time t4, human subject A presses start switch S and stands on platform 10, and after the measurement is taken, the measurement result is displayed. Human subject A then presses memory key M. As a result, CPU 110 stores measurement data x4 in rewritable memory 150c and lights up memory display area 120a.

Subsequently at Time t5, human subject B presses start switch S and stands on platform 10, but does not press memory key M after the measurement is taken. At Time t6, human subject C presses start switch S and stands on platform 10, but does not press memory key M after the measurement is taken. As a result, CPU 110 ends the measurement process without storing measurement data x5 or x6. Subsequently at Time t7, human subject A presses start switch S and difference key F. CPU 110 then reads from rewritable memory 150c measurement data x4 for display on display unit 120. What is displayed on display unit 120 will then change to the zero display, "0.00 kg", and when human subject A stands on platform 10, the weight of human subject A is measured. CPU 110 then obtains the difference between the current measurement result (measurement data x7) and the measurement data x4. Specifically, the difference data β2 is obtained by calculating β2=x7−x4.

In this example, given that the difference data β2 is within a range of ±20 kg, CPU 110 generates image data showing the difference data β2 expressed at the scale interval of 20 g and causes display unit 120 to display an image corresponding to the image data, thereby ending the process.

Memory display area 120a will be maintained in the lighted state because measurement data x4 of human subject A stored at Time t4 will be held in rewritable memory 150c even after the difference data β2 is obtained and the display is completed. Therefore, if difference key F is again pressed and a measurement is taken, the difference is again obtained based on the measurement data x4 as the base value.

On the other hand, in a case in which human subject A wishes to set another base value or in a case in which another human subject wishes to store measurement data x of this another human subject as the base value, measurement data x4 can be deleted, for example, by pressing memory key M when the power of measurement apparatus 100A is off. Memory display area 120a turns dark when the measurement data x4 is deleted.

As described in the foregoing, in the first embodiment in which measurement apparatus 100 that is not provided with memory key M, only the immediately previous measurement result can be used as the base value. However, according to measurement apparatus 100A of the present embodiment, measurement data xi specified by memory key M is used as the base value. That is, in a case in which measurements of the same human subject are taken at plural timings, the measurement result taken at the specified timing can be stored as the base value.

In a case in which a human subject does not wish to use the difference output function, the human subject merely presses start switch S to have a measurement taken, and therefore, otherwise unnecessary measurement data is not stored. Furthermore, in a case in which memory key M is pressed to effect the storage of the measurement data, memory display area 120a lights up. The memory display area 120a will be maintained in the lighted state as long as the measurement data is being stored, and the human subject can obtain the difference based on the same base value as many times as the human subject wishes as long as memory display area 120a is lighted. Other users, if they visually determine that memory display area 120a is lighted, will understand that the difference output function is not available at that moment; therefore, a situation can be avoided in which the difference between the measurement results of different human subjects is erroneously output.

B-1: Modifications of Second Embodiment

Modification 1

In the above embodiment, description has been given of a case in which memory key M is provided so that the desired measurement data xi is stored, i.e., memory key M serves as the storage instructor. However, difference key F may concurrently serve as the storage instructor. Specifically, a human subject may press start switch S and stand on platform 10 without pressing difference key F, and the measurement of weight is taken (Step Sc1 to Sc3; No to Sc5 of FIG. 8). In Step Sc7, a human subject presses difference key F instead of memory key M, so that the measurement data xi is stored.

According to this modification, only the particular measurement data xi can be stored in rewritable memory 150c without additionally providing memory key M. Thus, the same effects as in the second embodiment can be attained.

Modification 2

In the above embodiment, description has been given of a case in which memory key M is pressed after the weight is measured and in which the measurement result is stored as measurement data xi. However, memory key M may be pressed first and the weight may be measured thereafter, so that the measurement result is stored as measurement data xi.

Figure 10:
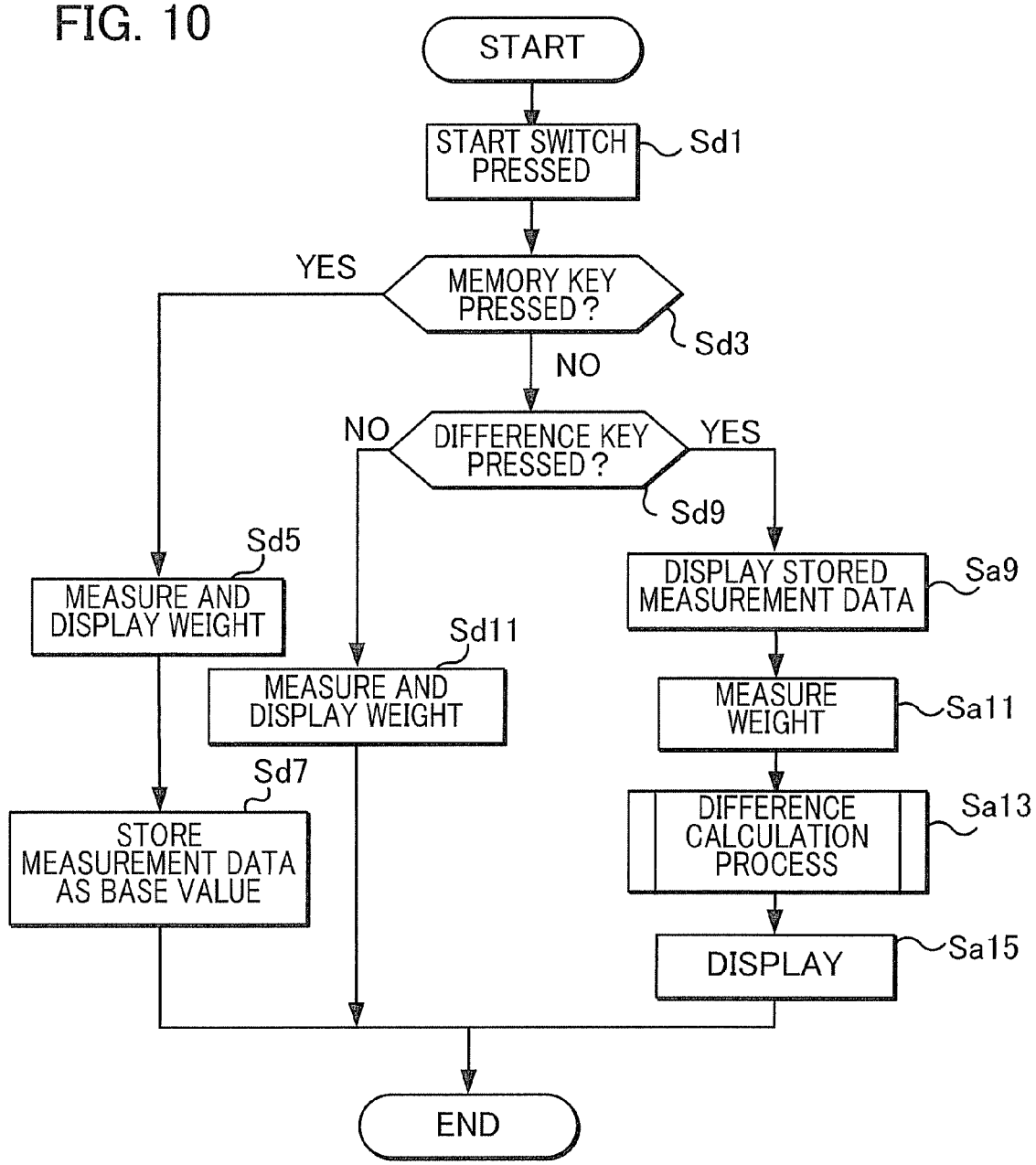
FIG. 10 is a flowchart showing a flow of operation according to a modification of the second embodiment.

FIG. 10 is a flowchart showing a flow of operation according to this modification. As shown in FIG. 10, in a case in which start switch S is first pressed (Step Sd1), measurement apparatus 100A is turned on. CPU 110 then determines whether memory key M is pressed (Step Sd3). In a case in which a result of the determination is affirmative, the weight of a human subject is measured (Step Sd5) after the human subject stands on platform 10. CPU 110 then stores the measurement result as the measurement data xi (Step Sd7).

On the other hand, in a case in which a result of the determination of Step Sd3 is negative, i.e., in a case in which memory key M is not pressed, CPU 110 subsequently determines whether difference key F is pressed (Step Sd9). In a case in which a result of the determination is negative, i.e., a human subject stands on platform 10 without having pressed difference key F, the weight of the human subject is measured, and a result of the measurement is displayed (Step Sd11). The measurement process is then completed. In a case in which a result of the determination of Step Sd9 is negative, i.e., difference key F is pressed, CPU 110 executes processes of Steps Sa9, Sa11, Sa13, and Sa15 as shown in FIG. 8, so that the difference is output (displayed). According to the present modification, the same effects as in the second embodiment can be attained.

C: Third Embodiment

FIGS. 11 to 14 are next referred to in order to describe a measurement apparatus 100B according to the third embodiment of the present invention.

The present embodiment differs from the first embodiment in that measurement apparatus 100B has individual keys for identifying human subjects. Furthermore, start switch S provided with measurement apparatus 100 of the first embodiment is not provided with measurement apparatus 100B of the present embodiment.

It should be noted that in each figure of FIGS. 11 to 14, the same reference numerals are assigned to the same components as those of the first embodiment, and the description thereof is omitted as appropriate.

Figure 11:
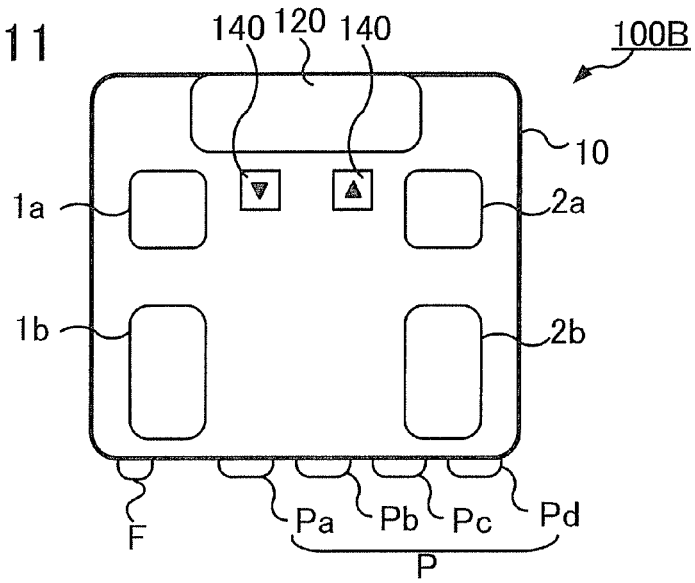
FIG. 11 is a plane view showing a measurement apparatus 100B according to a third embodiment of the present invention.
Figure 12:
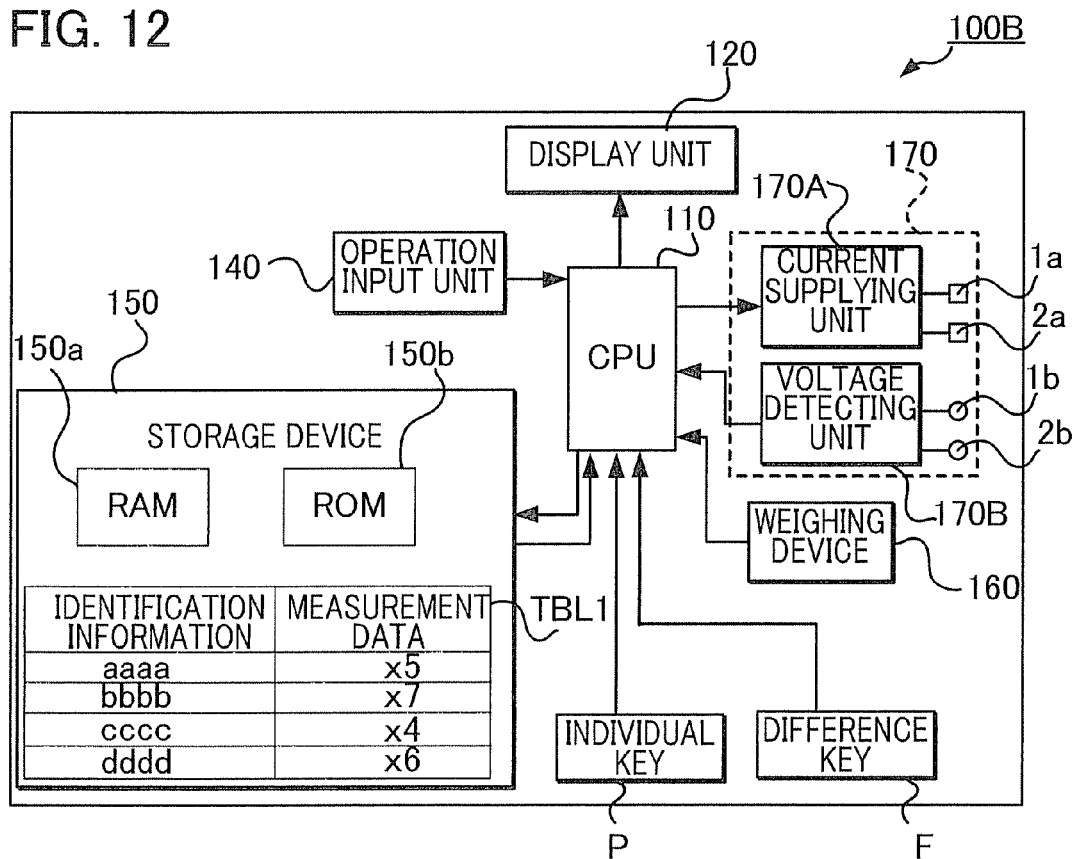
FIG. 12 is a block diagram showing an electrical configuration of measurement apparatus 100B.

FIG. 11 is a plane view showing an external view of measurement apparatus 100B of the present embodiment. FIG. 12 is a block diagram showing an electrical configuration of measurement apparatus 100B. As shown in FIGS. 11 and 12, measurement apparatus 100B has individual keys P (Pa, Pb, Pc, Pd) and difference key F. Each individual key P is an identifier (identifying means) for identifying a human subject. Specifically, in a case in which a human subject presses one of individual keys Pa, Pb, Pc, and Pd, CPU 110 of measurement apparatus 100 identifies a human subject based on identification information corresponding to the pressed individual key P. Furthermore, individual key P also serves as a start switch for turning on measurement apparatus 100B.

As shown in FIG. 12, there is provided an individual table TBL1 in memory storage device 150 of measurement apparatus 100B. There are stored in individual table TBL1 measurement data xi corresponding to identification information of each human subject. Every time a measurement is taken of a human subject, measurement data xi corresponding to the identification information indicating the human subject is overwritten by a new measurement result. Thus, measurement data xi of each human subject stored in individual table TBL1 is always updated to the latest value.

Figure 13:
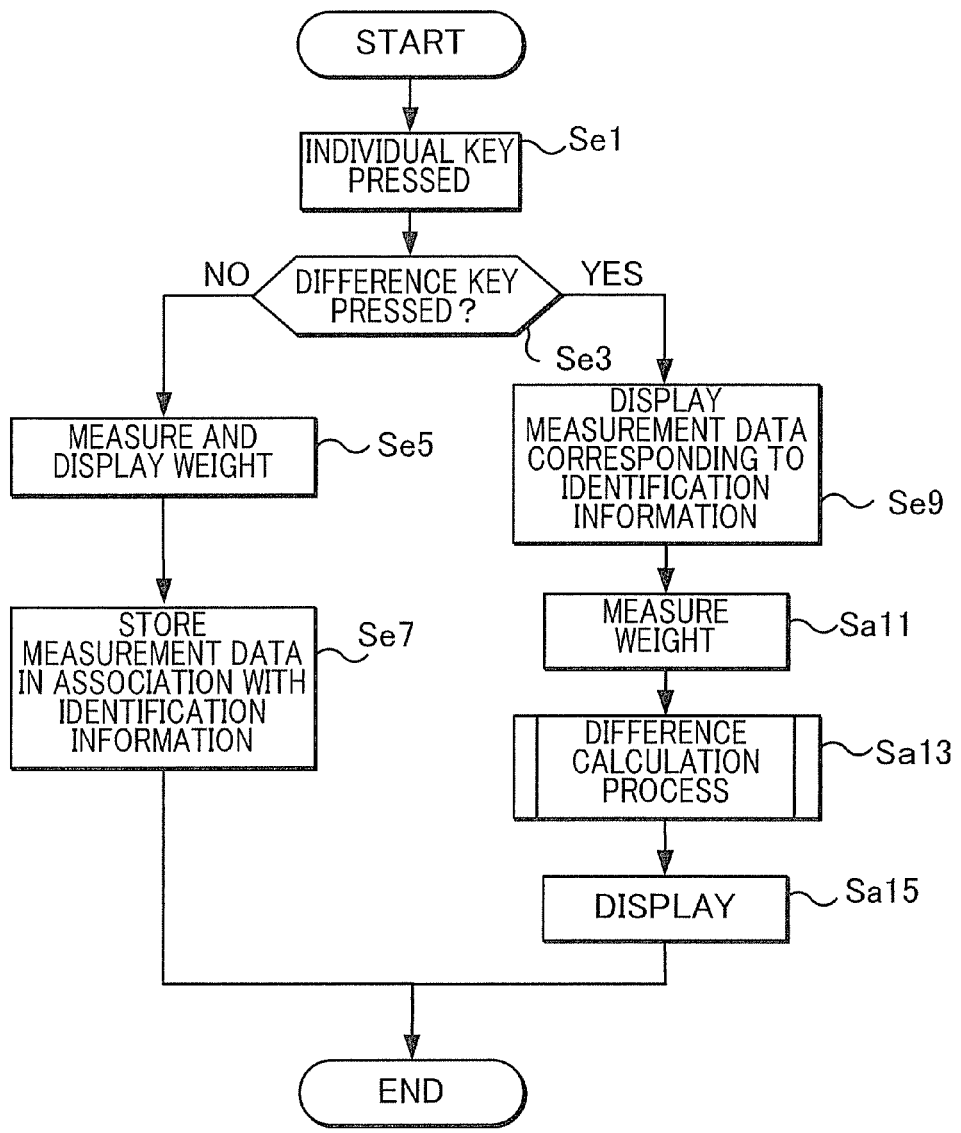
FIG. 13 is a flowchart showing a flow of operation according to the present embodiment.

FIG. 13 is a flowchart showing a flow of operation according to the present embodiment. As shown in FIG. 13, in Step Se1, in a case in which one of individual keys P is pressed, measurement apparatus 100B is turned on. CPU 110 subsequently determines whether difference key F is pressed (Step Se3). In a case in which a result of the determination is negative, and a human subject stands on platform 10, CPU 110 measures the weight of the human subject and displays the result of the measurement (Step Se5). CPU 110 subsequently overwrites the measurement data xi in association with identification information corresponding to individual key P pressed in Step Se1 in individual table TBL1 (Step Se7).

On the other hand, in a case in which a result of the determination of Step Se3 is affirmative, i.e., difference key F is pressed, CPU 110 refers to individual table TBL1 to read measurement data xi corresponding to the identification information corresponding to the pressed individual key P to display the read measurement data xi on display unit 120 (Step Se9). Subsequently, the display will turn to the zero display, "0.00 kg", and, in a case in which the human subject stands on platform 10, CPU 110 measures the weight of the human subject (Step Sa11) and executes the difference calculation process (FIG. 5) (Step Sa13).

In the difference calculation process, as shown in FIG. 4, in Step Sb1, CPU 110 reads the calculation equation (difference=comparison value−base value) from ROM 150b. Subsequently, CPU 110 assigns in the calculation equation the current measurement result measured in Step Sa11 as the comparison value and assigns the measurement data xi read from individual table TBL11 in Step Se9 as the base value, thereby obtaining the difference βp (Step Sb1). Subsequently, CPU 110 displays on display unit 120 an image represented by image data obtained by executing the processes of Steps Sb3 to Sb9 of FIG. 4 (Step Sa15 of FIG. 13), thereby ending the measurement process.

There may be a situation in which plural human subjects use the difference output function at a gym or a health club. In such a situation, after a human subject (human subject A) has the first measurement taken, another human subject (human subject B) may use the same measurement apparatus before the human subject A performs the second measurement. However, in the present embodiment, an individual key P is assigned to each of the plural human subjects, and identification information indicating each individual key P is stored in association with the base value in individual table TBL1. Therefore, according to the present embodiment, even in a case in which human subject B uses the same measurement apparatus after human subject A performs the first measurement and before the second measurement, a situation can be avoided in which the difference between the measurement result of human subject A and that of human subject B is erroneously obtained.

Figure 14:
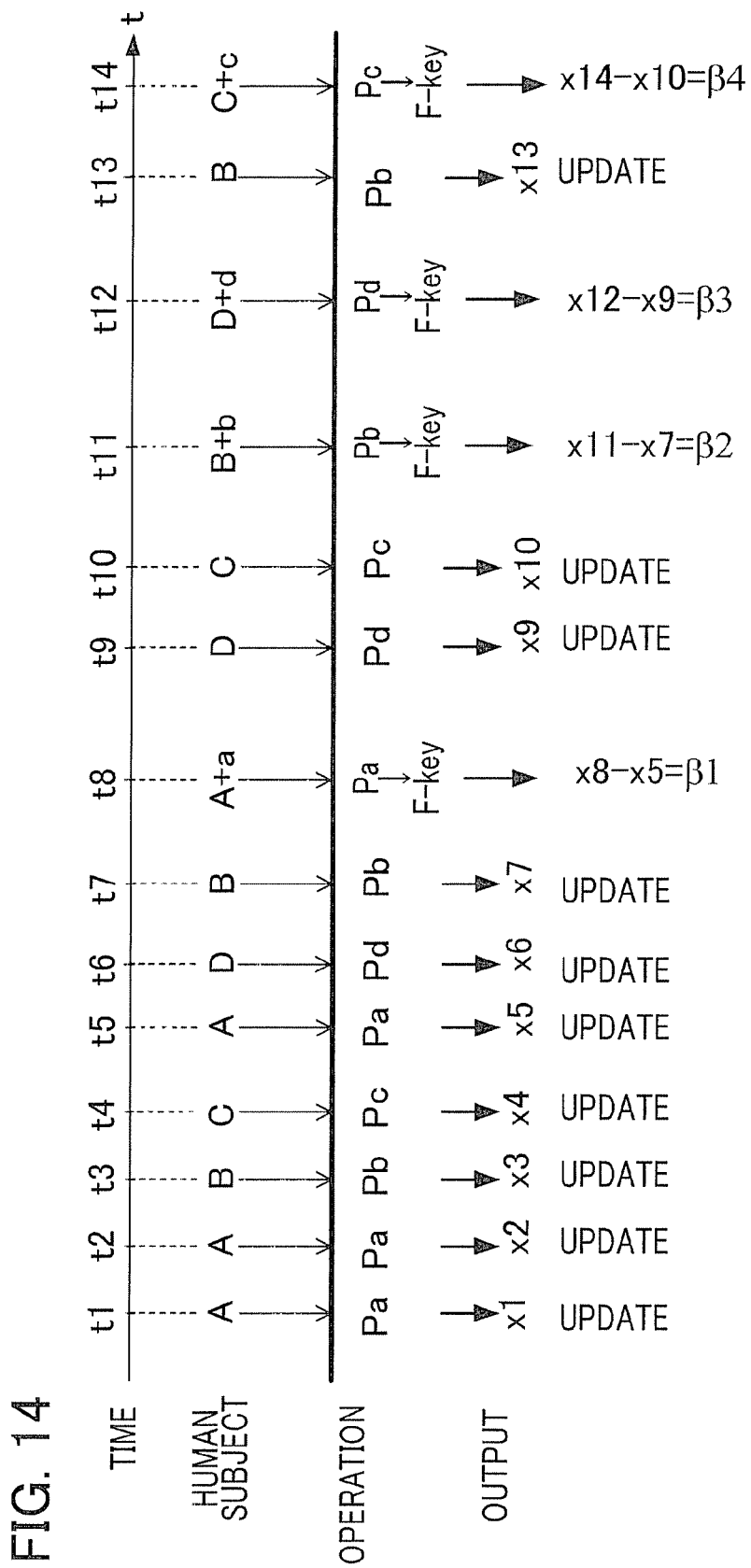
FIG. 14 is a time chart for describing how a measurement process of the present embodiment is performed.

FIG. 14 is a time chart showing how measurements are performed at measurement apparatus 100B of the present embodiment. As shown in FIG. 14, at Time t1, human subject A first presses individual key Pa and stands on platform 10. As a result, measurement data x1 is stored in association with identification information "aaaa" corresponding to individual key Pa in individual table TBL1. Subsequently at Time t2, human subject A again presses individual key Pa and stands on platform 10, and as a result, in individual table TBL1, measurement data x1 corresponding to identification information "aaaa" is updated to measurement data x2. Similarly, at Time t3, a human subject B presses individual key Pb and stands on platform 10, whereby in individual table TBL1, measurement data x3 is stored in association with identification information "bbbb" corresponding to individual key Pb. At Time T4, a human subject C presses individual key Pc and stands on platform 10, whereby in individual table TBL1, measurement data x4 is stored in association with identification information "cccc" corresponding to individual key Pc. Thus, measurement data that is stored in association with identification information corresponding to individual key P that is pressed each Time ti is updated in individual table TBL1. After Time t7, individual table TBL1 will be updated to that shown in FIG. 12. Specifically, measurement data x5 is stored in association with identification information "aaaa"; measurement data x7 in association with identification information "bbbb"; measurement data x4 in association with identification information "cccc"; and measurement data x6 in association with identification "dddd".

Subsequently at Time t8, human subject A presses difference key F after pressing individual key Pa. CPU 110 then refers to individual table TBL1 to read measurement data x5 corresponding to identification information "aaaa" indicating individual key Pa, for display on display unit 120. After a predetermined time period passes, the display is turned to the zero display "0.00 kg". When human subject A stands on platform 10, CPU 110 obtains measurement data x8 indicating the current measurement result. CPU 110 then assigns measurement data x5 to the base value of the calculation equation and assigns the measurement data x8 to the comparison value, to obtain the difference β1 through difference β1=x8−x5.

Subsequently at Time t9, human subject D presses the individual key Pd and stands on platform 10, so that measurement data x6 is updated to measurement data x9. At Time t10, human subject C presses the individual key Pc and stands on platform 10, so that measurement data x4 is updated to measurement data x10. Subsequently at Time t11, when human subject B presses difference key F after pressing individual key Pb and stands on platform 10, the difference between measurement data x7 stored in association with identification information "bbbb" and measurement data x11 indicating the current measurement result is obtained (difference β2=x11−x7). Similarly, at Time t12, the difference β3=x12−x9 is obtained for human subject D; and at Time t14, the difference β4=x14−x10 is obtained for human subject C.

As described in the foregoing, according to measurement apparatus 100B of the present embodiment, the same effects as those in the first embodiment can be attained. Furthermore, in a case in which human subjects A, B, C, and D use the same measurement apparatus, the difference calculation process is performed on an individual basis. Specifically, because measurement data xi is stored and updated in correspondence with identification information indicating each human subject in individual table TBL1, even when, after human subject A stores the measurement data in individual table TBL1, another human subject has a measurement taken before human subject A instructs the difference output, the difference calculation process between the current measurement data xi of the other human subject and the stored previous measurement data xi of human subject A will not be erroneously performed. Therefore, even in a situation in which plural human subjects use the same measurement apparatus, individuals can be identified without error, and the difference calculation process can be performed for each individual.

D: Fourth Embodiment

FIGS. 15 to 18 are now referred to in order to describe a measurement apparatus 100C according to the fourth embodiment of the present invention. The present embodiment differs from the above third embodiment in that measurement apparatus 100C has a memory key M.

In FIGS. 15 to 18, the same reference numerals are used for the same components as those in the third embodiment, and description thereof will be omitted as appropriate.

Figure 15:
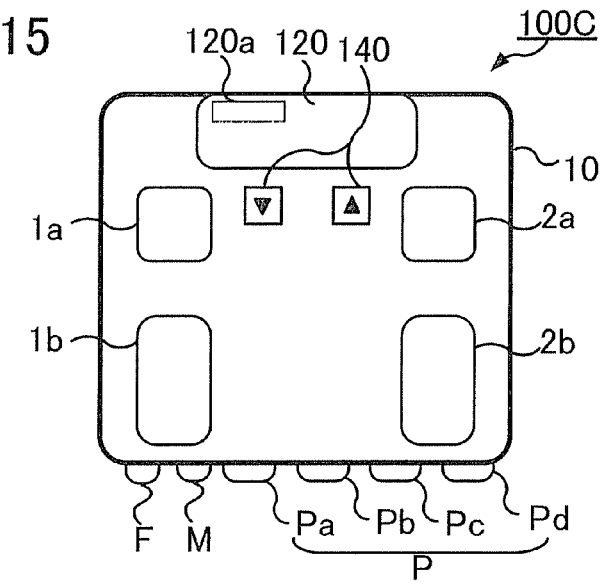
FIG. 15 is a plane view showing a measurement apparatus 100C according to a fourth embodiment of the present invention.
Figure 16:
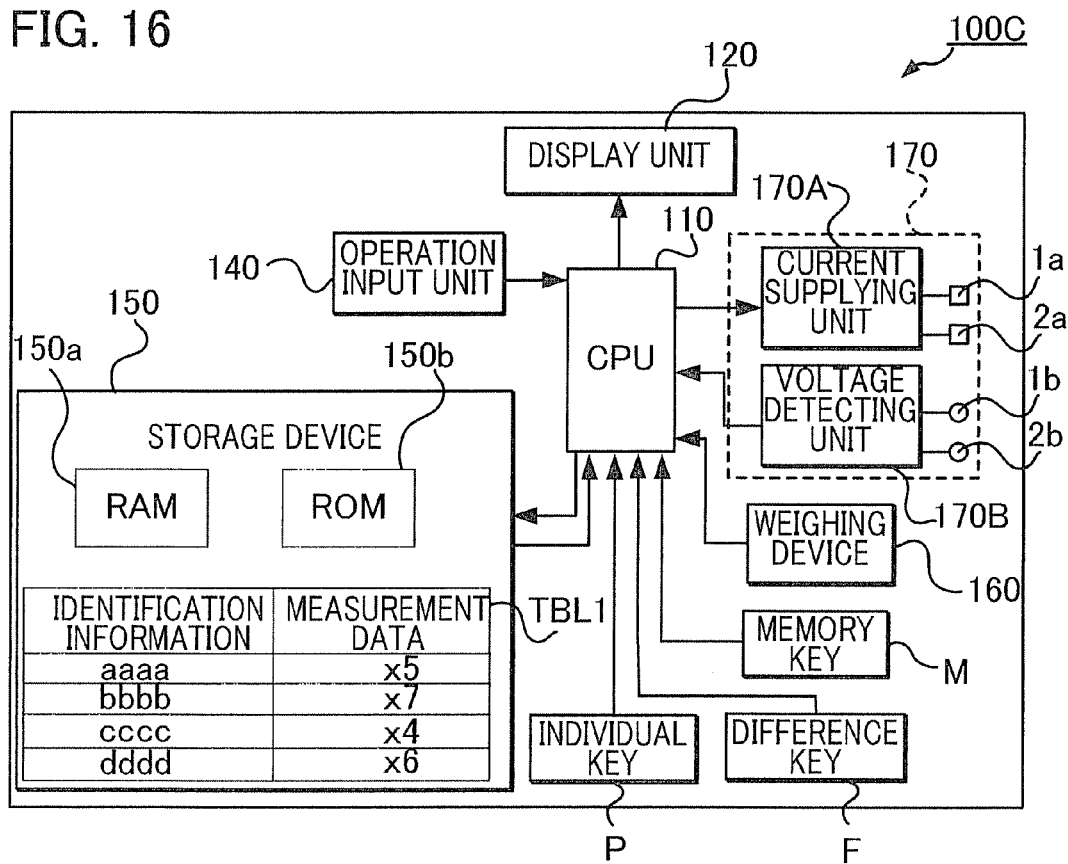
FIG. 16 is a block diagram showing an electrical configuration of measurement apparatus 100C.
Figure 18:
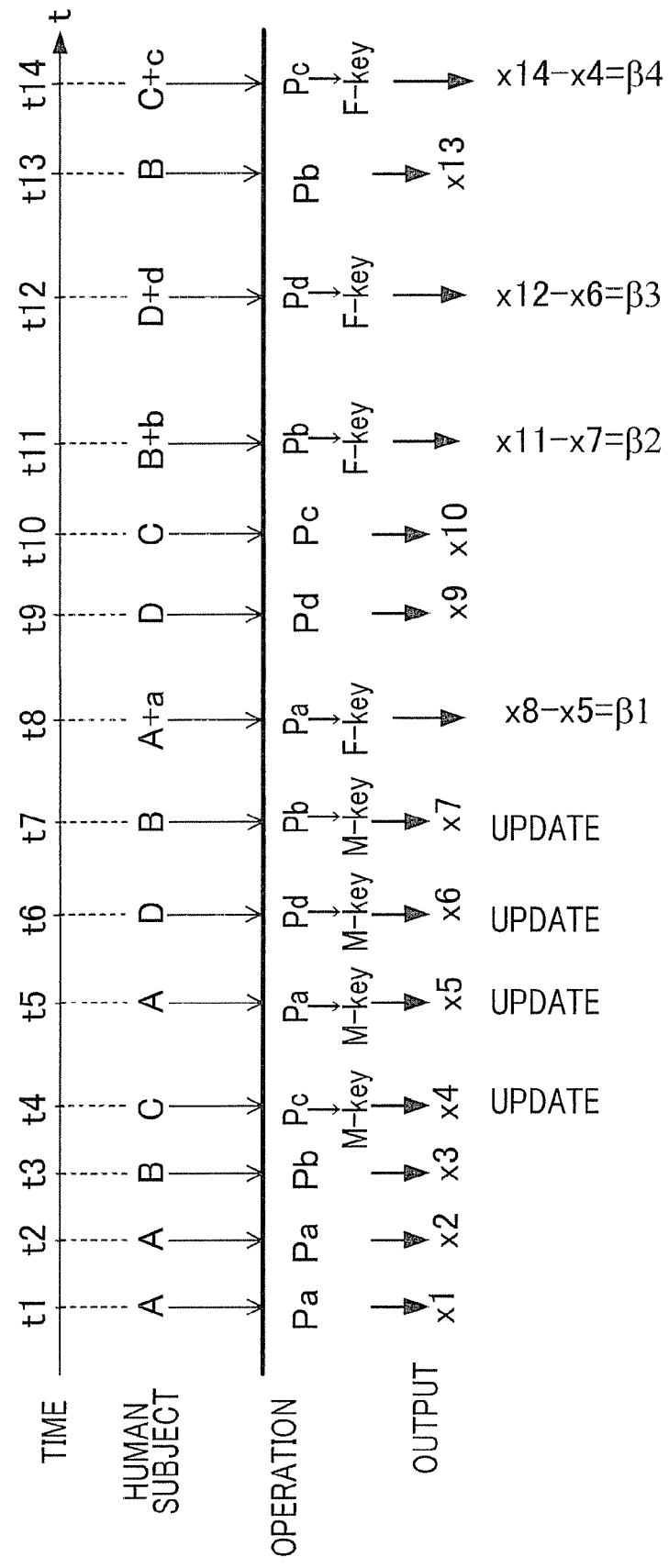
FIG. 18 is a time chart for describing how a measurement process of the present embodiment is performed.

FIG. 15 is a plane view showing an external view of measurement apparatus 100C according to the fourth embodiment. FIG. 16 is a block diagram showing an electrical configuration of measurement apparatus 100C. FIG. 18 is a time chart for describing how measurements are performed at measurement apparatus 100C. As shown in FIGS. 15 and 16, measurement apparatus 100C is provided with memory key M in addition to difference key F and individual keys P. In a case in which memory key M is pressed after the weight is measured, the measurement data xi indicating the measurement result is stored in individual table TBL1 in association with identification information indicating that individual key P was pressed before the measurement was taken. In other words, only measurement data xi showing the weight measured when memory key M was pressed is stored in individual table TBL1. Therefore, as shown in FIG. 18, in a case in which measurements are performed at each of Times t1 to t7, only measurement data x4, x5, x6, and x7 are stored in individual table TBL1, the measurement data x4, x5, x6, and x7 showing values measured at Time t4, t5, t6, and t7 at which memory key M was pressed. Therefore, memory key M serves as a storage instructor (storage instruction means) that instructs the measurement apparatus to store particular measurement data xi as the base value in individual table TBL1.

Figure 17:
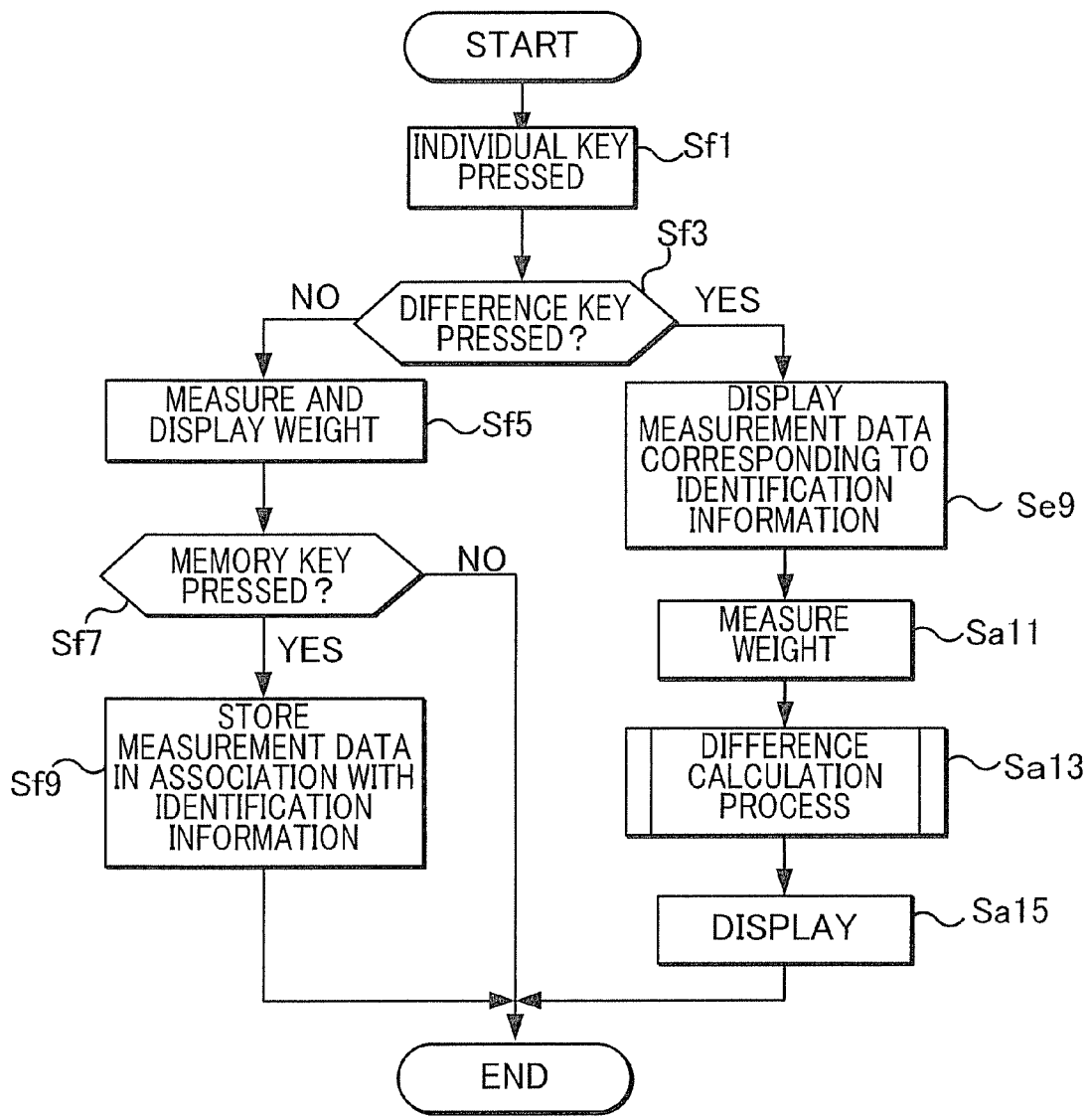
FIG. 17 is a flowchart showing a flow of operation according to the present embodiment.

FIG. 17 is a flowchart showing a flow of operation according to the present embodiment. As shown in FIG. 17, in Step Sf1, in a case in which one of individual keys P is pressed, measurement apparatus 100C is turned on. CPU 110 then determines whether difference key F is pressed (Step Sf3). In a case in which a result of the determination is negative, and when a human subject stands on platform 10, the weight of the human subject is measured, and a result of the measurement is displayed on display unit 120 (Step Sf5). Subsequently, CPU 110 determines whether memory key M is pressed (Step Sf7). In a case in which a result of the determination is negative, i.e., memory key M is not pressed, CPU 110 ends the measurement process.

On the other hand, in a case in which a result of the determination of Step Sf7 is affirmative, i.e., memory key M is pressed, and CPU 110 stores in individual table TBL1 measurement data xi in association with identification information indicating that individual key P was pressed in Step Sf1.

In a case in which a result of the determination of Step Sf3 is affirmative, i.e., difference key F is pressed, CPU 110 reads measurement data xi corresponding to identification information indicating individual key P pressed in Step Sf1, from among one or more measurement data xi stored in individual table TBL1, for display on display unit 120. The display will then turn to the zero display "0.00 kg" (Step Se9). When a human subject stands on platform 10, the weight of the human subject is measured (Step Sa11), and CPU 110 then executes the difference calculation process (FIG. 4) (Step Sa13). Subsequently, in Step Sa15, an image showing the difference βp is displayed on display unit 120.

Specifically, provided that the difference βp is within the range of ±20 kg, CPU 110 generates image data representing the difference data in the scale interval of 20 g, and CPU 110 causes display unit 120 to display an image represented by the image data, thereby ending the process.

As an alternative to the exemplary flow of FIG. 17, the determination as to whether memory key M has been pressed may be performed before the determination difference key D has been pressed, in the same manner as described in FIG. 10. Specifically, after Step Sf1 of FIG. 17, it is first determined whether memory key M has been pressed as in Sd3 of FIG. 10. In a case in which a result of the determination is affirmative, CPU 110 stores the measurement result in association with identification information indicating individual key P that was pressed in Step Sf1 in individual table TBL1 instead of simply storing the measurement result in rewritable memory 150c as in Step Sd7 of FIG. 10. In a case in which a result of the determination as to whether memory key M has been pressed is negative, it is then determined whether difference key D has been pressed as in Step Sd9 of FIG. 10. In a case in which a result of the determination of Step Sd9 is negative, CPU 110 simply displays a measurement result to end the measurement process. In a case in which a result of the determination of Step Sd9 is affirmative, Steps Se9, Sa11, Sa13, and Sa15, as shown in FIG. 17, will be performed.

FIG. 18 is next referred to in order to describe how measurements are performed at measurement apparatus 100C.

As shown in FIG. 18, at Time t1, human subject A first presses individual key Pa and stands on platform 10, and the measurement data x1 is displayed on display unit 120, completing the measurement process. At Time t2, human subject A again presses individual key Pa and stands on platform 10, and measurement data x2 is displayed on display unit 120, and the measurement process is completed. Subsequently at Time t3, a human subject B presses individual key Pb and stands on platform 10, and measurement data x3 is displayed on display unit 120, and the measurement process is completed.

Subsequently at Time t4, a human subject C presses individual key Pc and stands on platform 10 and presses memory key M after the measurement is taken. As a result, in individual table TBL1, measurement data x4 is stored in association with identification information "cccc" indicating individual key Pc. Subsequently at Time t5, human subject A presses individual key Pa and stands on platform 10 and presses memory key M after the measurement is taken. In individual table TBL1, measurement data x5 is stored in association with identification information "aaaa" indicating individual key Pa. Thus, measurement data xi is updated only in a case in which both individual key P and memory key M are pressed. As a result, what is stored in individual table TBL1 at Time t7 is updated to what are shown in FIG. 16. Specifically, measurement data x5 is stored in association with identification information "aaaa"; measurement data x7 in association with identification information "bbbb"; measurement data x4 in association with identification information "cccc"; and measurement data x6 in association with identification information "dddd".

Subsequently at Time t8, in a case in which human subject A presses difference key F after pressing individual key Pa, CPU 110 refers to individual table TBL1 to read measurement data x5 that is stored in association with identification information "aaaa" indicating individual key Pa, to be displayed on display unit 120. After a predetermined time has elapsed, the display will turn to the zero display "0.00 kg".

Subsequently, when human subject A stands on platform 10, CPU 110 obtains measurement data x8 showing the measurement result. CPU 110 then assigns measurement data x5 as the base value and measurement data x8 as the comparison value to the calculation equation and obtains the difference through β1=x8−x5.

Subsequently, at Time t9, if human subject D presses individual key Pd and stands on platform 10, measurement data x9 is displayed on display unit 120. Because memory key M is not pressed, the stored data in individual table TBL1 is not overwritten, i.e., measurement data x6 remains stored in association with identification information "dddd". Similarly at Time t10, if human subject C presses individual key Pc and stands on platform 10, measurement data x10 is displayed on display unit 120, but the data in individual table TBL1 is not overwritten.

At Time t12, if human subject D presses difference key F after pressing individual key Pd, the difference between measurement data x6 stored in association with identification information "dddd" and measurement data x12 showing the current measurement result is obtained (difference β3=x12−x6). Thus, memory key M is used to identify the measurement result to be stored, thereby allowing human subject D to obtain the difference between the current measurement result and measurement result (i.e., measurement data x6) measured at a desired timing (Time t6) instead of the difference between the current measurement result and the immediately previous measurement result (measurement data x9) of human subject D.

As described in the foregoing, according to the present embodiment, the same effects as those of the third embodiment are obtained. Specifically, because a human subject is identified by individual key P, the difference calculation will not be performed between measurement results of different human subjects. Furthermore, as in the second embodiment, in measurement apparatus 100C of the present embodiment, the measurement data xi specified by memory key M is used as the base value, whereas in a case in which no memory key M is provided, only the latest measurement data can be used as the base value. In other words, in a case in which a human subject has plural measurements taken, the measurement result at the specified timing can be stored as the base value.

E: Modifications

Modification 1

In the first to the fourth embodiments, description was given of cases in which the difference calculation process is used for obtaining the difference in measured weights. However, the difference calculation process may be performed for other indices relating to body compositions, such as the ratio of body fat. For example, in measurement apparatus 100 of the first embodiment, CPU 110 stores the measured (estimated) ratio of body fat % Fat in rewritable memory 150c every time a measurement is taken of a ratio of body fat of a human subject. In a case in which a human subject presses difference key F and has another measurement of ratio of body fat taken, the difference is obtained between the measurement result at that time and the base value stored in rewritable memory 150c. According to this modification, the same effects as those of the above embodiment can be attained.

CPU 110 estimates the ratio of body fat % Fat in accordance with the following equation:

$$\%Fat = f1 * Z * W/H^2 - f2 \qquad \text{Equation (1)}$$

in which f1 and f2 are constants and are determined by multiple regression analysis as appropriate, Z is bioelectrical impedance, W is weight, and H is height. "Height" is a parameter for generating ratio of body fat % Fat and is input from a touch panel of display unit 120 as individual data of a human subject.

In the first term of Equation (1), "$W/H^2$" is a body mass index (BMI) and shows the degree of obesity. The constants f1 and f2 of Equation (1) are derived through multiple regression analysis based on ratio of body fat obtained through the DXA (Dual energy X-ray Absorptiometry) ratio of body fat. The DXA method uses two types of X-ray beams of different wavelengths to measure the body compositions of humans based on the amount of transmitted radiation. The DXA method is capable of measuring body fat ratio with high accuracy; however, it requires a large device, and a human subject is inevitably exposed to radiation, although the amount of radiation is very small. However, according to the bioelectrical impedance method used in the present embodiment, an easy and safe estimation of body fat ratio % Fat is made possible.

Modification 2

In the above third and fourth embodiments and the above modification, individual key P is used to identify a human subject. Alternatively, an identification code unique to each human subject may be assigned, so that a human subject can input the identification code through the touch panel of display unit 120. In this modification, a number of identification codes can be used to store the base values of a number of human subjects in individual table TBL1. Therefore, the present modification is better suited to a case in which a large number of human subjects use the same measurement apparatus, for example, at a gym, a health club, or a public path, in comparison with the above embodiment in which the limited number of individual keys P is used.

Modification 3

In the third and fourth embodiments and the above modifications, individual keys or identification codes are used to identify a human subject. However, biometric information showing the characteristics of a human subject may be stored for each human subject, and CPU 110 may determine, based on the stored biometric information, whether a human subject for the previous measurement corresponds to a human subject for the current measurement taken after difference key F is pressed. Specifically, in the third embodiment, when weight to be used as the base value is measured, the biometric information of the human subject is measured and is stored in individual table TBL1 in association with the base value. In a case in which difference key F is pressed at a later timing and the measurement of weight is taken, the biometric information of the human subject is measured, and the measured biometric information is compared with the biometric information stored in individual table TBL1. CPU 110 then selects, from among plural sets of measurement data xi stored in individual table TBL1, measurement data xi having the same biometric information as the base value, and the difference calculation process is then executed. The biometric information used for identifying a human subject is physical information unique to individuals and can be one of the indices relating to body composition, such as the ratio of body fat that can be measured by measurement apparatus 100B or 100C. Furthermore, more than one set of biometric information may be used to identify a human subject. According to the present modification, a human subject need not press an individual key or input an identification code, and therefore, the convenience for the user is increased.

Modification 4

In the first to fourth embodiments, measurement data xi is updated every time weight is measured. However, measurement data xi may be stored in correspondence with a measured time. Specifically, measurement apparatus 100, 100A, 100B, or 100C may be further provided with a timer (not shown) for keeping the current time. CPU 110, when storing measurement data xi in rewritable memory 150c or in individual table TBL1, obtains the current time from the timer to store the measurement data xi in association with the obtained current time (or in association with the obtained current time and identification information in the case of individual table TBL1). CPU 110 obtains, in a case in which difference key F is pressed, the latest measurement data xi from rewritable memory 150c or individual table TBL1 as the base value. It is to be noted that CPU 110 performs an interrupt service at a certain time interval, thereby to delete, from rewritable memory 150c or individual table TBL1, older measurement data xi that is stored in association with the time from which a certain period has elapsed. Alternatively, measurement data xi that is older may be deleted in a case in which the storage capacity in rewritable memory 150c or individual table TBL1 is exceeded.

What is claimed is:

1. A measurement apparatus having a measurer that measures an index relating to body compositions of a human subject, comprising:
   a memory storage device that stores a measurement result of the measurer;
   an identifier that uniquely identifies each of plural human subjects by identification information;
   a storage instructor that instructs the measurement apparatus to store in the memory storage device a measurement result measured by the measurer as the base value;
   a difference output instructor that instructs the measurement apparatus to output difference between a previous measurement result and a current measurement result, the previous measurement result measured by the measurer being a base value and the current measurement result measured by the measurer being a comparison value; and
   a difference outputter that, in a case in which the measurement apparatus is instructed to output the difference by the difference output instructor and in a case in which one of the plural human subjects is specified by the identifier, reads from the memory storage device a measurement result that has been stored in association with the specified identification information as the base value and that calculates the difference between the base value and the comparison value,
   wherein, only in a case in which the measurement apparatus is instructed by the storage instructor to store a measurement result measured by the measurer and in a case in which one of the plural human subjects is specified by the identifier, will the memory storage device store the measurement result in association with the specified identification information, and
   wherein the storage instructor comprises a memory key in common for all of the plural human subjects, and the identifier comprises an individual key corresponding to each of the plural human subjects.

2. A measurement apparatus according to claim 1, wherein the difference outputter includes a displayer that displays the difference on the display unit, and wherein the displayer displays the difference in a first scale interval in a case in which the difference falls within the predetermined range, whereas the displayer displays the difference in a second scale interval that is larger than the first scale interval in a case in which the difference is outside the predetermined range.

* * * * *